United States Patent
Johnson

(10) Patent No.: US 7,456,170 B2
(45) Date of Patent: *Nov. 25, 2008

(54) TRIAZOLOBENZODIAZEPINES AND THEIR USE AS VASOPRESSIN ANTAGONISTS

(75) Inventor: Patrick S. Johnson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/570,694

(22) PCT Filed: Aug. 12, 2005

(86) PCT No.: PCT/IB2005/002711

§ 371 (c)(1),
(2), (4) Date: Feb. 6, 2007

(87) PCT Pub. No.: WO2006/021882

PCT Pub. Date: Mar. 2, 2006

(65) Prior Publication Data

US 2007/0249585 A1    Oct. 25, 2007

Related U.S. Application Data

(60) Provisional application No. 60/616,601, filed on Oct. 5, 2004.

(30) Foreign Application Priority Data

Aug. 25, 2004  (GB) .................. 0418980.9

(51) Int. Cl.
*A61P 15/12* (2006.01)
*A61K 31/5517* (2006.01)
*C07D 487/04* (2006.01)

(52) U.S. Cl. ...................... 514/220; 540/564

(58) Field of Classification Search ............. 514/220; 540/564

See application file for complete search history.

(56) References Cited

U.S. PATENT DOCUMENTS 7,119,088 B2 * 10/2006 Bryans et al. ............... 514/220

2006/0194794 A1 * 8/2006 Bryans et al. ............... 514/220
2007/0027328 A1 * 2/2007 Aronhime et al. ........... 548/537

FOREIGN PATENT DOCUMENTS

WO  WO 9906409     2/1999
WO  WO 2004074291  9/2004

OTHER PUBLICATIONS

Kakefunda, et al., *Bioorganic & Medicinal Chemistry*, "Discovery of 4,5-Diphenyl-1,2,4-triazole Derivatives as a Novel Class of Selective antagonists for the Human $V_{1A}$ receptor", vol. 10, pp. 1905-1912 (2002).

* cited by examiner

*Primary Examiner*—Brenda L Coleman
(74) *Attorney, Agent, or Firm*—Gregg C. Benson; John A. Wichtowski

(57)    ABSTRACT

Compounds of formula (I),

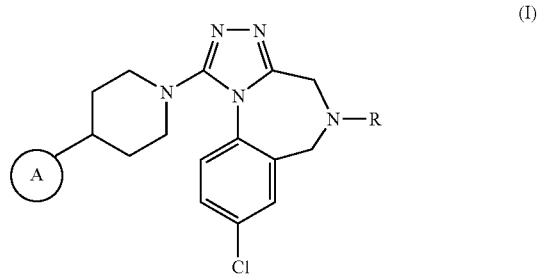

or pharmaceutically acceptable derivatives thereof, wherein
R represents H, $C_{1-6}$ alkyl, $SO_2R^1$, $SO_2NR^1R^2$, or $COR^1$;
$R^1$ and $R^2$ independently represent $C_{1-6}$ alkyl; and
Ring A represents a phenyl ring or a pyridinyl ring;
may be useful in the treatment of anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor and Raynaud's disease.

9 Claims, No Drawings

TRIAZOLOBENZODIAZEPINES AND THEIR USE AS VASOPRESSIN ANTAGONISTS

This application is a national stage entry under 35 U.S.C. § 371 of PCT/IB05/002711, filed Aug. 12, 2005 which claims benefit of Provisional Application No. 60/616,601, filed Oct. 5, 2004.

This invention relates to novel compounds useful in therapy and to processes for the preparation thereof. It also relates to intermediates used in the preparation of such compounds, compositions containing such compounds and their uses.

The compounds of the present invention have been found to have useful pharmaceutical properties. They may be used to treat aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis.

Particularly of interest are the following diseases or disorders: anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor and Raynaud's disease.

In particular, they exhibit vasopressin antagonistic activity and can be used in the treatment of dysmenorrhoea (primary and secondary).

There is a high unmet need in the area of menstrual disorders and it is estimated that up to 90% of all menstruating women are affected to some degree. Up to 42% of women miss work or other activties due to menstrual pain and it has been estimated that around 600 million work hours a year are lost in the US as a result (costing around $2 billion in lost productivity).

Menstrual pain in the lower abdomen is caused by myometrial hyperactivity and reduced uterine blood flow. These pathophysiological changes result in abdominal pain that radiates out to the back and legs. This may result in women feeling nauseous, having headaches and suffering from insomnia. This condition is called dysmenorrhoea and can be classified as either primary or secondary dysmenorrhoea.

Primary dysmenorrhoea is diagnosed when no abnormality causing the condition is identified. This affects up to 50% of the female population. Where an underlying gynaecological disorder is present, such as endometriosis, pelvic inflammatory disease (PID), fibroids or cancers, secondary dysmenorrhoea will be diagnosed. Secondary dysmenorrhoea is diagnosed in only approximately 25% of women suffering from dysmenorrhoea. Dysmenorrhoea can occur in conjunction with menorrhagia, which accounts for around 12% of referrals to gynaecology outpatients departments.

Currently, women suffering from primary dysmenorrhoea are treated with non-steroidal anti-inflammatory drugs (NSAID's) or the oral contraceptive pill. In cases of secondary dysmenorrhoea surgery may be undertaken to correct the underlying gynaecological disorder.

Women suffering from dysmenorrhoea have circulating vasopressin levels which are greater than those observed in healthy women at the same time of the menstrual cycle. Inhibition of the pharmacological actions of vasopressin, at the uterine vasopressin receptor, may prevent dysmenorrhoea.

According to the present invention there are provided compounds of formula (I),

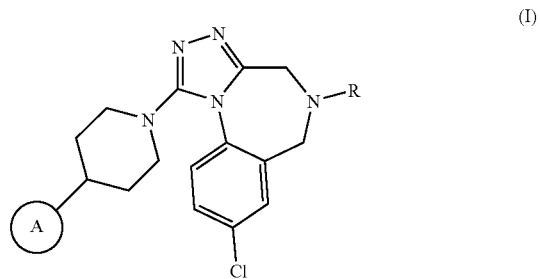

or pharmaceutically acceptable salts, solvates, esters or amides thereof, wherein R represents H, $C_{1-6}$ alkyl, $SO_2R^1$, $SO_2NR^1R^2$, or $COR^1$;
$R^1$ and $R^2$ independently represent $C_{1-6}$ alkyl; and
Ring A represents a phenyl ring or a pyridinyl ring.

Alkyl groups containing the requisite number of carbon atoms, except where indicated, can be unbranched or branched chain. Examples include methyl, ethyl, n-propyl, i-propyl, n-butyl, i-butyl, sec-butyl and t-butyl.

In a preferred embodiment

Preferred aspects of the definition of the compounds of formula (I) above are as follows:

(i) compounds according to formula (I) wherein R is $C_{1-6}$ alkyl;
(ii) compounds according to aspect (i) wherein R is methyl;
(iii) compounds according to formula (I) wherein R is H:
(iv) compounds according to formula (I) wherein R is $SO_2R^1$;
(v) compounds according to formula (I) wherein R is $COR^1$;
(vi) compounds according to formula (I) wherein R is $SO_2NR^1R^2$;
(vii) compounds according to any of aspects (iv) to (vi) wherein $R^1$ is methyl;
(viii) compounds according to aspect (vi) wherein $R^2$ is methyl;
(ix) compounds according to formula (I) or any of aspects (i) to (viii) wherein Ring A is phenyl.
(x) compounds according to formula (I) or any of aspects (i) to (viii) wherein Ring A is pyridinyl.

Preferred compounds according to the present invention are:

8-Chloro-1-(4-pyridin-2-ylpiperidin-1-yl)-5,6-dihydro-4H-[1,2,4]triazolo[4,3-a][1,4]benzodiazepine;
8-Chloro-5-methyl-1-(4- pyridin-2-ylpiperidin-1-yl)-5,6-dihydro-4H-[1,2,4]triazolo[4,3-a][1,4]benzodiazepine;

8-Chloro-5-(methylsulfonyl)-1-(4-pyridin-2-ylpiperidin-1-yl)-5,6-dihydro-4H-[1,2,4]triazolo[4,3-a][1,4]benzodiazepine;

8-Chloro-5-methyl-1-(4-phenylpiperidin-1-yl)-5,6-dihydro-4H-[1,2,4,]triazolo[4,3-a][1,4]benzodiazepine;

8-Chloro-1-(4-phenylpiperidin-1-yl)-5,6-dihydro-4H-[1,2,4]triazolo[4,3-a][1,4]benzodiazepine;

8-Chloro-5-(methylsulfonyl)-1-(4-phenylpiperidin-1-yl)-5,6-dihydro-4H-[1,2,4]triazolo[4,3-a][1,4]benzodiazepine;

5-Acetyl-8-chloro-1-(4-phenylpiperidin-1-yl)-5,6-dihydro-4H-[1,2,4]triazolo[4,3-a][1,4]benzodiazepine; and 8-Chloro-N,N-dimethyl-1-(4-phenylpiperidin-1-yl)-4H-[1,2,4]triazolo[4,3-a][1,4]benzodiazepine-5(6H)-sulfonamide.

The pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, D- and L-lactate, malate, maleate, malonate, mesylate, methylsulphate, naphthylate, 2-napsylate, nicotinate, nitrate, orotate, oxalate, palmitate, palmoate, phosphate, hydrogen phosphate, dihydrogen phosphate, saccharate, stearate, succinate, sulphate, D- and L-tartrate, tosylate and trifluoroacetate salts. A particularly suitable salt is the besylate derivative of the compounds of the present invention.

Suitable base salts are formed from bases, which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts see Stahl and Wermuth, Handbook of Pharmaceutical Salts: Properties, Selection and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components what may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (I) and pharmaceutically acceptable derivatives include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labelled compounds of formula (I).

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, hydrolytic cleavage. Such derivatives are referred to as "prodrugs". Further information on the use of prodrugs may be found in "Pro-drugs as Novel Delivery Systems, Vol. 14, ACS Symposium Series (T Higuchi and W Stella) and "Bioreversible Carriers in Drug Design", Pergamon Press, 1987 (ed. E B Roche, American Pharmaceutical Association).

Prodrugs in accordance with the invention can, for example, be produced by replacing appropriate functionalities present in the compounds of formula (I) with certain moieties know to those skilled in the art as "pro-moieties" as described, for example, in "Design of Prodrugs" by H Bundgaard (Elsevier 1985).

Finally, certain compounds of formula (I) may themselves act as prodrugs of other compounds of formula (I).

Also within the scope of the invention are the metabolites of the compounds of formula (I) when formed in vivo.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible, and where the compound contains, for example, a keto or oxime group or an aromatic moiety, tautomeric isomerism ('tautomerism') may occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral HPLC.

Alternatively, the racemate (or racemic precursor) may be reacted with a suitable optically active compound, for example, an alcohol, or, in the case where the compounds of formula (I) contains an acidic or basic, moiety, an acid or base such as tartaric acid or 1-phenylethylamine. The resulting diastereomeric mixture may be separated by chromatography and/or fractional crystallisation and one or both of the diastereomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention also includes all pharmaceutically acceptable isotopic variations of a compound of the formula (I) one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulphur such as $^{35}S$, fluorine such as $^{18}F$, iodine such as $^{123}I$ and $^{125}I$, and chlorine such as $^{36}Cl$.

Certain isotopically-labelled compounds of formula (I), for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Pharmaceutically acceptable solvates in accordance with the invention include those wherein the solvent of crystallisation may be isotopically substituted, e.g. $D_2O$, $d_6$-acetone and $d_6$-DMSO.

According to the present invention there is also provided a process for the production of a compound of formula (I), which comprises:

reacting a compound of formula (II)

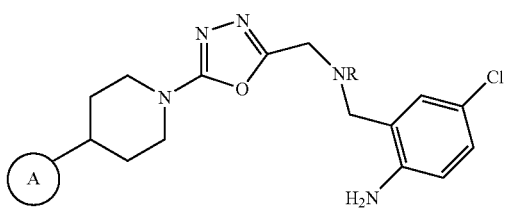

(II)

with an acid catalyst; wherein ring A and R are as defined above.

According to the present invention there is also provided a process for the production of a compound of formula (I), which comprises:

reacting a compound of formula (II)

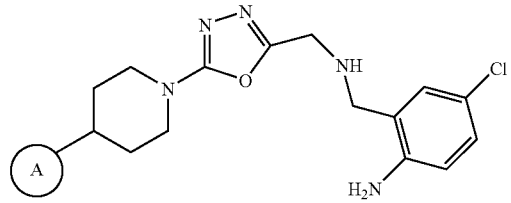

(II)

with an acid catalyst, followed by coupling with halide (IV)

(IV)

wherein ring A and R are as defined above.

According to the present invention there is also provided a process for the production of a compound of formula (I), which comprises:

reacting a compound of formula (III)

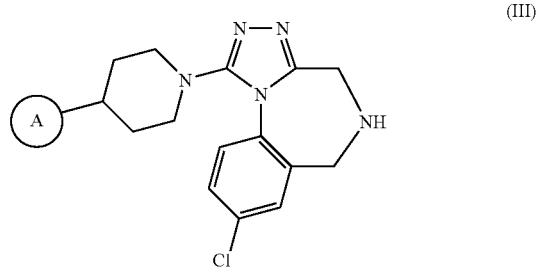

(III)

with aldehyde or ketone (V)

=O            (V)

wherein ring A and R are as defined above.

According to the present invention there is also provided a process for the production of a compound of formula (I), which comprises:

reacting a compound of formula (XVII)

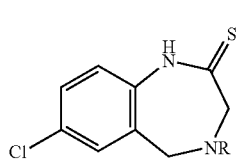

(XVII)

with a compound of formula (IX)

(IX)

wherein ring A and R are as defined above.

According to the present invention there is also provided a process for the production of a compound of formula (I), which comprises:

reacting a compound of formula (XVIII)

(XVIII)

with a compound of formula (IX)

(IX)

wherein ring A and R are as defined above.

According to the present invention there is also provided a process for the production of a compound of formula (I), which comprises:

deprotecting a compound of formula (XXVIII)

(XXVIII)

followed by cyclisation of the resulting product with base;
wherein Ring A, R, Prot and LG are as defined above.
Unless otherwise provided herein:
WSCDI means 1-(3-dimethylaminopropyl)-3-ethylcarbodiimide hydrochloride;
DCC means N,N'-dicyclohexylcarbodiimide;
HOAT means 1-hydroxy-7-azabenzotriazole;
HOBT means 1-hydroxybenzotriazole hydrate;
PyBOP® means Benzotriazol-1-yloxytris(pyrrolidino)phosphoniumhexafluorophosphate;
PyBrOP® means bromo-tris-pyrrolidino-phosphonium-hexafluoro phosphate;
HBTU means O-Benzotriazol-1-yl-N,N,N'N'-tetramethyluronium hexafluoro-phosphate.
Mukaiyama's reagent means 2-chloro-1-methyl pyridinium iodide;
KHMDS means potassium bis(trimethylsilyl)amide;
Hünig's base means N-ethyldiisopropylamine;
$Et_3N$ means triethylamine;
HMDS means hexamethyldisilazane
Dba means dibenzylideneacetone;
Boc means tert-butoxycarbonyl;
CBz means benzyloxycarbonyl;
p-TSA means p-toluenesulphonic acid
TBAF means tetra-butyl ammonium fluoride
TBDMSCl means tert-butyldimethylchlorosilane
TMSCl means chlorotrimethylsilane
MsCl means methanesulfonyl chloride
$NaBH(OAc)_3$ means sodium triacetoxyborohydride
MeOH means methanol, EtOH means ethanol, and EtOAc means ethyl acetate, $Et_2O$ means diethyl ether; THF means tetrahydrofuran and DCM means dichloromethane, DMF means N,N-dimethylformamide;
MeOTs means methyl 4-methylbenzenesulfonate
AcOH means acetic add, TFA means trifluoroacetic acid;
Me means methyl, Et means ethyl;
Cl means chloro; and
OH means hydroxy.

The following schemes illustrate the preparation of compounds of the formula (I), throughout which Ring A and R are as defined above unless otherwise stated.

Scheme 1.1

(II)

(I)

Step (a): Oxadiazole (II) is reacted in the presence of an acid catalyst to give the compound of formula (I). Typically the reaction is carried out by heating the starting materials to elevated temperatures, such as 50 to 150° C., for 1 to 48 hours with a suitable acid catalyst such as p-TSA, trifluoroacetic acid or Lewis acid catalyst such as magnesium chloride, optionally using a solvent such as xylene, toluene or tetrahydrofuran.

Alternatively, compounds of formula (I) may be prepared according to Scheme 1.2.

Scheme 1.2

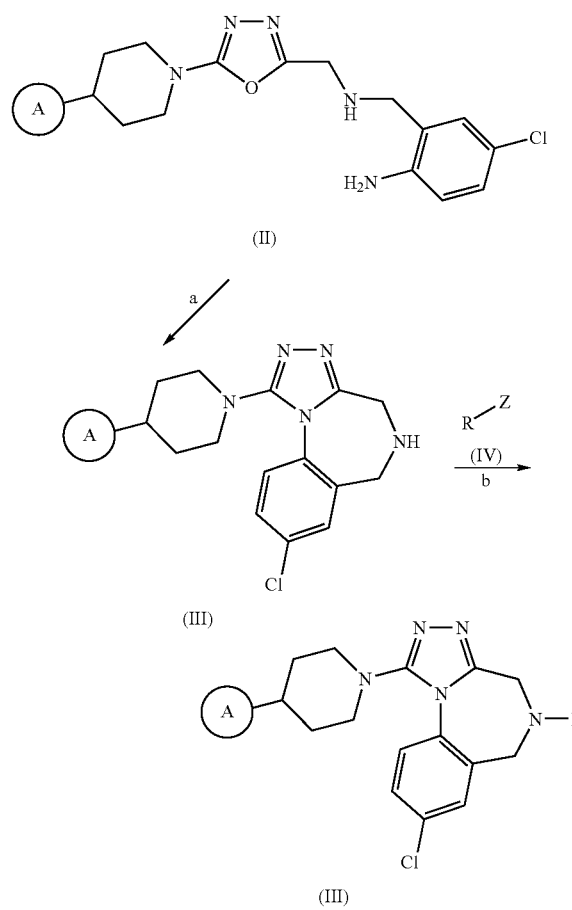

(II)

(III)

(III)

Z is halo, typically Cl

Compounds suitable for use as compound (IV) are commercially available or are known in the literature.

Step (b): The reaction of amine (III) with compound (IV) can be carried out by standard methods.

When R=SO$_2$R$^1$ or SO$_2$NR$^1$R$^2$ then, typically, the coupling may be undertaken by using:

(i) a sulfamyl/sulfonyl chloride (IV) and amine (III) with an excess of acid acceptor, in a suitable solvent.

Acylation: R=COR$^1$, Z=Cl (i) An excess of acid chloride (IV) (generated in-situ), 1 eq. of amine (III), optionally with an excess of 3° amine such as Et$_3$N, Hünig's base or NMM, in DCM or THF, without heating for 1 to 24 hours. The preferred conditions are: amine (V), 1.2 eq. R$^1$COCl in Et$_3$N in DCM at 0° C. for 45 minutes.

or, (ii) Amine (III) may be treated with an anhydride (R$^1$CO)$_2$O optionally with an excess of 3° amine such as Et$_3$N, Hünig's base or NMM, in DCM or THF and heated for 1 to 24 hours. Preferred conditions are: amine (III), 1.2 eq. Anhydride (R$^1$CO)$_2$O, 1.5 eq. Et$_3$N in dichloromethane at 0° C. for 2 hours.

Alkylation: R=alkyl (optionally substituted), Z=halo (preferably Br or I)

Alkylation of compound (III) can be performed by reaction with a suitable alkylating agent, RZ in the presence of a suitable tertiary amine (NMM, Et$_3$N or Hünig's base) or alkali metal base (K$_2$CO$_3$, Cs$_2$CO$_3$) in a suitable solvent (MeCN, DMF), optionally with heating at 30 to 120° C. Preferred conditions are: amine (III), 1.5 eq. MeI, 2.0 eq. K$_2$CO$_3$ in MeCN for 2 hours at room temperature.

Alternatively, when R=alkyl, compounds (I) may be prepared by the route shown below in Scheme 1.3.

Scheme 1.3

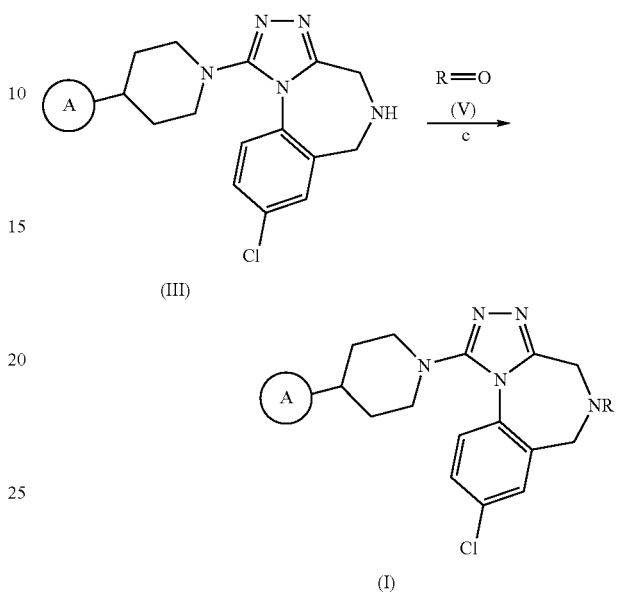

(III)

(I)

Compounds suitable for use as compound (V) are commercially available or are known in the literature.

Step (c): Amine (III) is reacted with an excess of suitable aldehyde/ketone in the presence of a reducing agent, such as sodium triacetoxyborohydride or sodium cyanoborohydride, to give the compound of formula (I). This reaction may be carried out by:

(i) stirring the starting materials at temperatures such as 20° C. to 80° C., for 1 to 48 hours in a suitable solvent such as dichloromethane, or, (ii) heating amine (III) with excess compound (V) with a suitable Lewis acid catalyst such as titanium tetrachloride or titanium tetraisopropoxide at temperatures such as 50° C. to 100° C. in a suitable solvent such as dichloroethane or ethanol, for 1 to 18 hours. Followed by reduction of the intermediate imine/iminium species with a suitable reducing agent, such as sodium borohydride, or hydrogenolysis over a suitable catalyst, such as platinum oxide or palladium on carbon.

Compounds suitable for use as compounds (II) are known in the literature or can be prepared as shown in Scheme 1.4 below.

Scheme 1.4

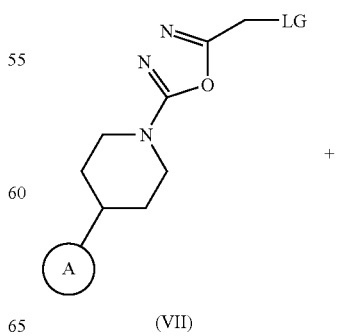

(VII)

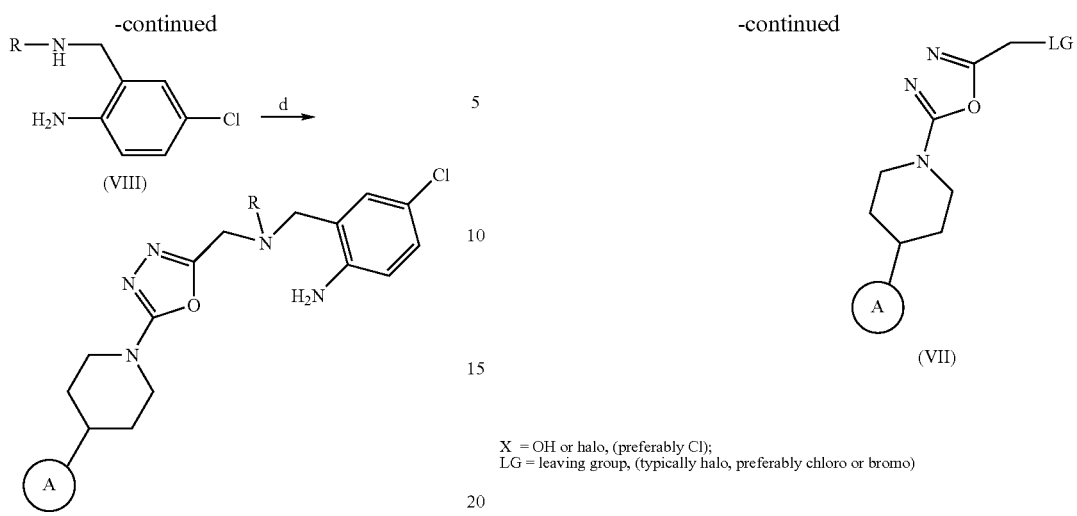

LG represents a leaving group, typically halo, and preferably chloro or bromo.

Compounds suitable for use as compounds (VIII) are known in the literature or can be prepared using standard methodology: for example, reduction of benzonitriles or nitrobenzenes.

Step (d): Compound (VII) is reacted with an excess of compound (VIII) to give compound (II), optionally in the presence of an excess of base, such as triethylamine, Hünig's base or NMM or potassium carbonate as proton acceptor, optionally in the presence of a catalyst (e.g. NaI) in a suitable high boiling solvent such as THF, Toluene or DMF at temperatures from 50° C. to 100° C., for 1 to 48 hours.

Compounds suitable for use as compound (VII) are known in the literature or can be prepared as shown in Scheme 1.5.

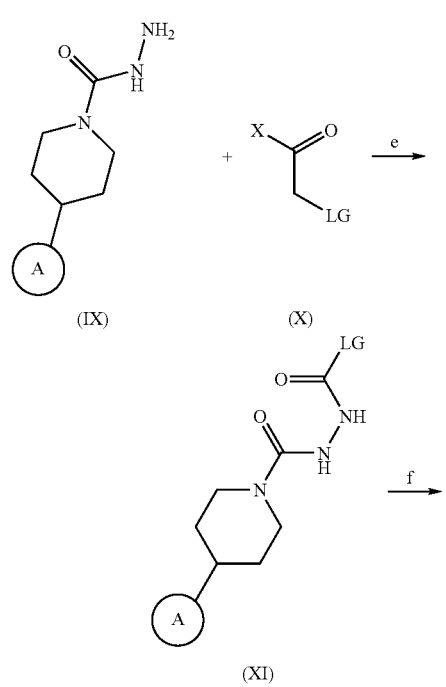

X = OH or halo, (preferably Cl);
LG = leaving group, (typically halo, preferably chloro or bromo)

Compound (X) is either commercially available or is known in the literature.

Step (e): The reaction of hydrazide (IX) with compound (X) can be carried out by standard methods.

Coupling may be undertaken by using either:
(i) an acyl chloride (X) and hydrazide (IX) with an excess of acid acceptor in a suitable solvent;
or
(ii) acid (X) with a conventional coupling agent and hydrazide (IX), optionally in the presence of a catalyst, with an excess of acid acceptor in a suitable solvent.

Typically the conditions are as follows:
(i) acid chloride (X) (generated in-situ), an excess of hydrazide (IX), optionally with an excess of 3° amine such as $Et_3N$, Hünig's base or NMM, in DCM or THF, without heating for 1 to 24 hours;
or,
(ii) acid (X), WSCDI /DCC and HOBT /HOAT, an excess of hydrazide (IX), with an excess of NMM, $Et_3N$, Hünig's base in THE, DCM or THF, at room temperature for 4 to 48 hours;
or,
(iii) acid (X), PYBOP®/PyBrOP®/Mukaiyama's reagent, an excess of hydrazide (IX), with an excess of NMM, $Et_3N$, Hünig's base in THF, DCM or THF, at room temperature for 4 to 24 hours.

Step (f): Cyclisation of compound (XI) may be carried out under suitable dehydrating conditions, at elevated temperatures for up to 18 hours. Typically, dehydrating agents such as polyphosphoric acid, phosphorous oxychloride, triflic anhydride are used at temperatures from 20 to 120° C., for 5 minutes to 12 hours. Optionally, the reaction can be carried out in the presence of a base, such as pyridine, and suitable solvents, such as dichloromethane and acetonitrile. Alternatively, the oxadiazole (VIII) may be prepared according to the method of Rigo et. al. Synth. Commun. 16(13), 1665, 1986.

Compounds suitable for use as compounds (IX) are known in the literature or can be prepared as shown in Scheme 1.6.

Scheme 1.6

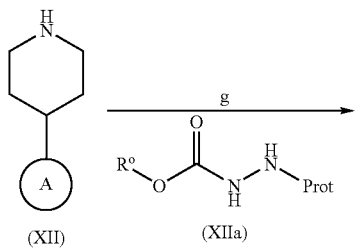

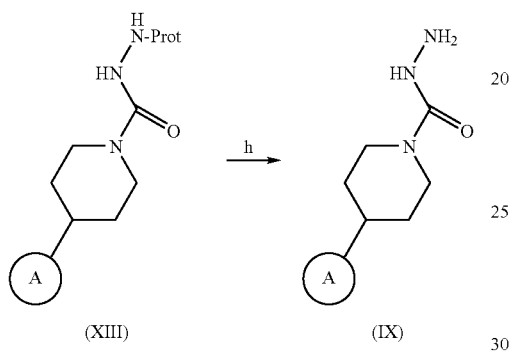

Prot = N protecting group;
R⁰ = is typically C1-2 alkyl

Compounds (XII) and (XIIa) are either commercially available or are known in the literature or may be prepared standard methodology.

Step (g): Amine (XII) and protected hydrazine (XIIa), where prot is typically Boc, may be coupled to give compound (XIII), typically by heating in a high boiling solvent for 1 to 48 hours, such as isopropylalcohol or THF. Then "prot" is removed using standard methodology as described in Step (h) to give (IX).

Step (h) Deprotection of compounds of formula (XIII) may be undertaken using standard methodology, as described in "Protecting Groups in Organic Synthesis" by T. W. Greene and P. Wutz." Preferred conditions when "Prot" is BOC are; excess 4M HCl/dioxane, in dioxane for about 2 hours at room temperature.

An alternative route to compound (IX) is shown below in Scheme 1.7:

Scheme 1.7

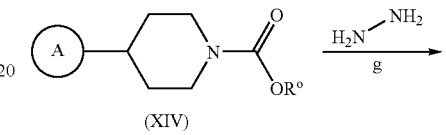

Ra is typically C1-2 alkyl

Step (g): The ester (XIV) may be reacted with hydrazine in a suitable solvent, such as methanol, at an elevated temperature to provide the hydrazide (IX).

Alternatively, compounds of formula (I) may be prepared according to Scheme 1.8 below:

Scheme 1.8

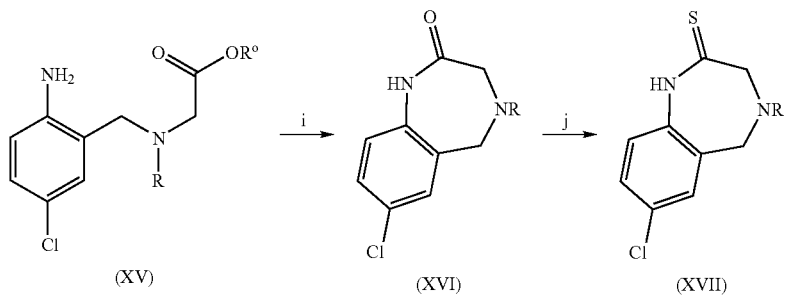

-continued

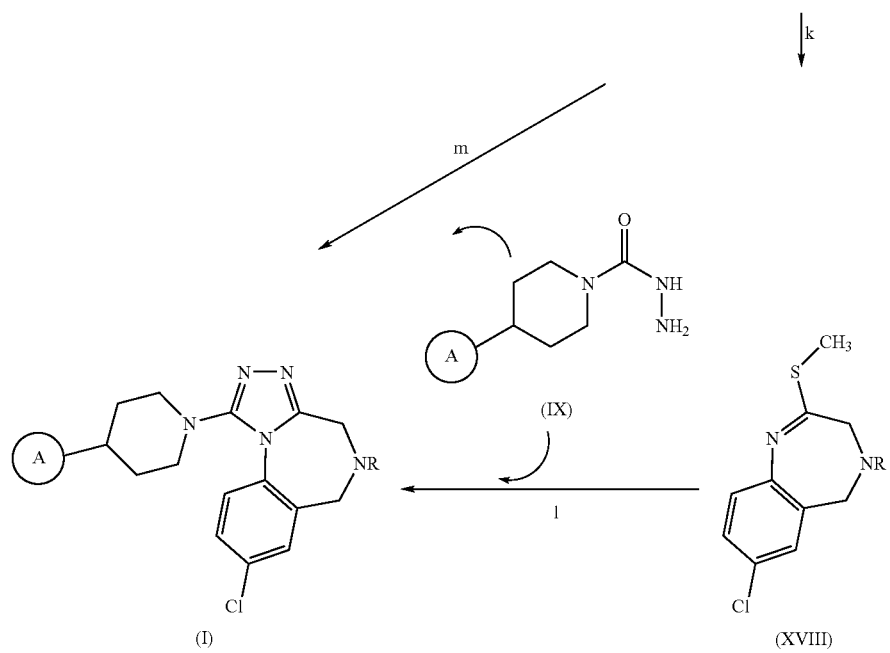

$R_b$ = H or $C_1$-$C_4$ alkyl, typically tert-butyl, methyl or ethyl

When R=H;

Step (i): Compounds of formula (XVI) may be prepared by an intra-molecular coupling of the amino acid (XV), with a conventional amide coupling agent, optionally with an excess of acid acceptor in a suitable solvent. Typically, amino acid (XV), WSCDI/DCC and HOBT/HOAT with excess 3° amine such as of NMM, $Et_3N$: Hünig's base in THF, DCM or THF, at room temperature for 4 to 48 hours.

When $R_b$=$C_1$-$C_4$ alkyl:

Step (i): Compounds of formula (XVI) may be prepared by base catalysed cyclisation of the amino ester (XV) typically carried out at room temperature or below for 1 to 5 hours. Typically, bases such as potassium tert-butoxide, sodium ethoxide or isopropyl magnesium chloride are used at or below 20° C. in a suitable solvent such as tetrahydrofuran or ethanol for 1 to 5 hours.

Step (j): Formation of Thioamide

Thionation of the amide (XVI) using a suitable thionating agent (e.g. Lawesson's reagent, $P_4S_{10}$), and optionally in the presence of a base such as $Na_2CO_3$, in a suitable solvent such as THF at between 0° C. and room temperature, provides the compound (XVII).

Step (k): Thioimidate formation

Treatment of the thioamide (XVII) with a strong base such as $KO^tBu$ or LDA, in a suitable solvent such as THF or ether, followed by quench of the anion formed by a suitable methylating agent such as MeI, Me p-tosylate, provides the thioimidate (XVIII).

Step (l): Triazole formation

The thioimidate (XVIII) is treated with the hydrazide (IX) in a suitable solvents typically ethanol at elevated temperature to provide the compound of formula (I), optionally in the presence of an acid catalysed such as TFA or p-TSA.

Step (m): The thioamide (XVII) is treated with the hydrazide (IX) in a suitable solvent, typically n-Butan-1-ol at elevated temperature to provide the compound of formula (I), optionally in the presence of an acid catalysed such as TFA or p-TSA.

Compounds of formula (I) may alternatively be prepared according to Scheme 1.9 below:

Scheme 1.9
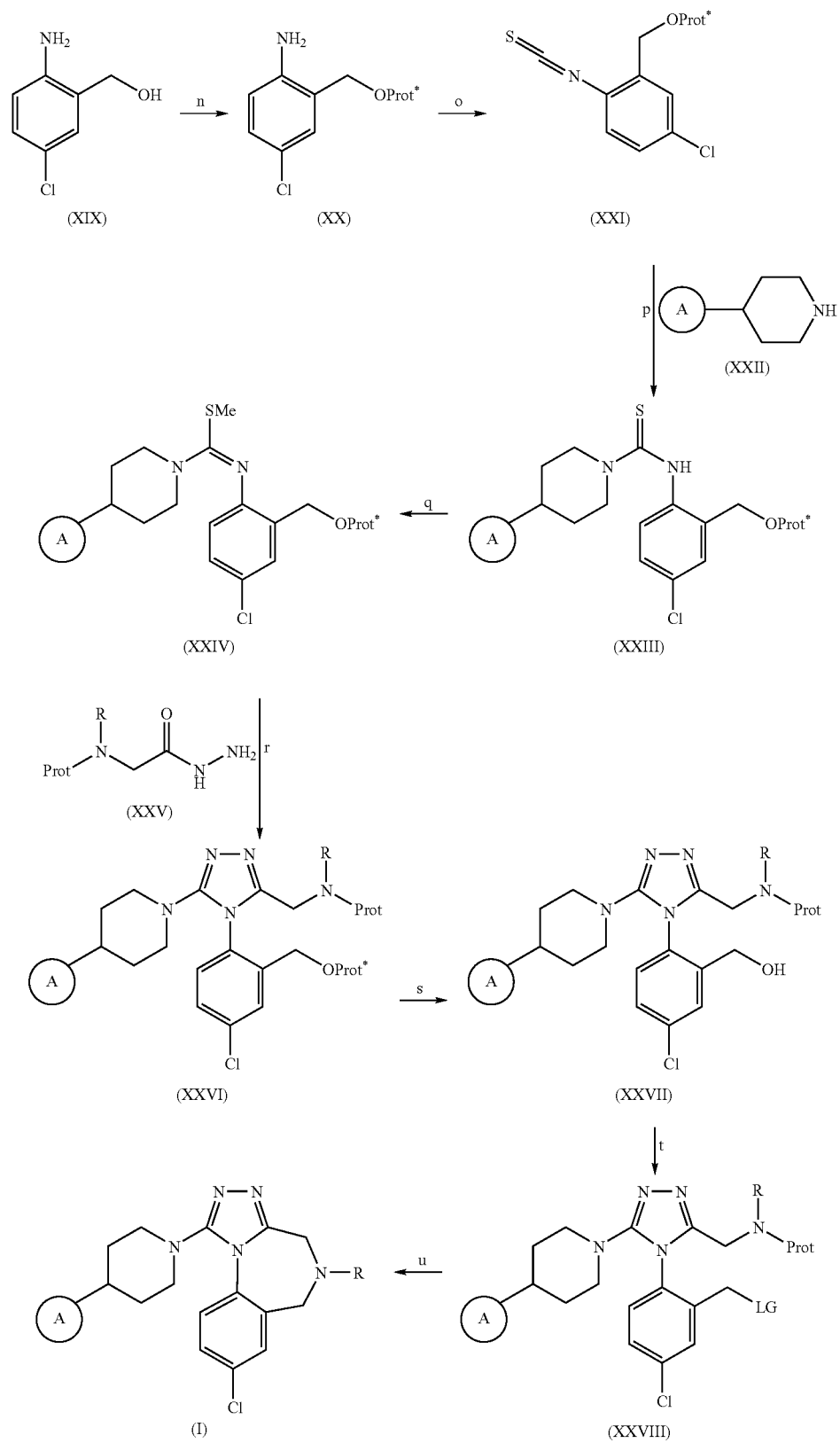
Prot = BOC;
Prot* = TBDMS;
LG = OMs; OTs

Step (n): Compound of formula (XIX) is protected with a suitable protecting group, (for example tert-butylsilyl group): using 1 eq. TBDMSCI, 1.1 eq., imidazole in a suitable high boiling solvent such as THF at room temperature for about 24 hours.

Step (o): Compound (XX) is reacted with thiophosgene to give compound (XXI), optionally in a suitable solvent such as THF, toluene or DMF at room temperature for about 24 hours. Preferred conditions: 1 eq. compound (XX), 1 eq. thiophosgene in THF at room temperature for 24 hours.

Step (p): Formation of Thioamide

Treatment of the isothiocyanate (XXI) with amine (XXII), in a suitable solvent such as EtOH at room temperature for 1 to 72 hours, provides the thioamide (XXIII). Preferred conditions: 1 eq. compound (XXII), 1 eq., isothiocyanate in EtOH at room temperature for 48 hours.

Step (q): This thioimidate formation may be undertaken as described in Step (k). Preferred conditions, 1 eq. compound (XXIII), 1 eq. KO$^1$Bu, 1 eq. MeOTs in THF at room temperature for about 15 minutes.

Step (r): The thioimidate (XXIV) is treated with hydrazide (XXV) (readily synthesized by treating its corresponding protected amino ester with hydrazine as described in Step (h)), to provide the compound of formula (XXVI). Preferred conditions: 1 eq. thioimidate (XXIV), 1.85 eq. hydrazide (XXV) in n-butan-1-ol at 120° C. in the presence of catalytic AcOH.

Step (s): Treatment of compound (XXVI) with TBAF, in a suitable solvent such as THF at room temperature for about 30 minutes, provides the compound of formula (XXVII).

Step (t): Compound (XVII) is converted to (XVIII) by treatment of compound (XVII) with MsCl or TsCl, in the presence of a suitable base such as Hünig's base or pyridine in a suitable solvent such as dichloromethane, at 0° C. to 25° C. for 5 to 120 minutes. Preferred conditions are: 1 eq. compound (XVII), 1.5 eq. Hünig's base, 1.2 eq. MsCl or TsCl in dichloromethne at 0° C. for 30 minutes.

Step (u) Compound of formula (XXVIII) is first deprotected by heating to elevated temperatures, such as 30 to 50° C., for 2 to 24 hours with acids such as HCl or TFA in a suitable solvent such as dioxane or DCM. Cyclisation to give compounds of formula (I) is then achieved by treatment with base such as Et$_3$N or Na$_2$CO$_3$ in a suitable solvent such as aqueous dioxane.

Compounds suitable for use as compounds (XV) are known in the literature or can be prepared using standard methodology, for example see C. Apfel et. al., J. Med. Chem. 44(12), 1847-1852, 2001, C. P. Lang et. al., WO2002008228, F. Ishikawa, J. Med. Chem. 28(10), 1387-93 1985 or Uskokovic, M. et. al., Journal of Organic Chemistry (1965), 30(9), 3111-14.

It will be apparent to those skilled in the art that sensitive functional groups may need to be protected and deprotected during synthesis of a compound of formula (I). This may be achieved by conventional techniques, for example as described in "Protective Groups in Organic Synthesis" by T W Greene and P G M Wuts, John Wiley and Sons Inc, 1991.

The compounds of the present invention are useful because they possess pharmacological activity in animals. In particular they are useful in the treatment of a number of conditions including aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis sleep disorder, spinal cord injury, thrombosis, urogenital tract infection, urolithiasis. Particularly of interest is dysmenorrhoea (primary or secondary), more particularly, primary dysmenorrhoea.

Thus, according to another aspect of the invention, there is provided a method of treatment of dysmenorrhoea which comprises administering a therapeutically effective amount of a compound of the invention to a patient suffering from anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease. The use of the compounds as a medicament and the use of the compounds of the present invention in the manufacture of a medicament for the treatment of anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease, particularly dysmenorrhoea, are also provided.

Compounds of the invention intended for pharmaceutical use may be administered as crystalline or amorphous products. They may be obtained, for example, as solid plugs, powders, or films by methods such as precipitation, crystallisation, freeze drying, spray drying, or evaporative drying. Microwave or radio frequency drying may be used for this purpose.

They may be administered alone or in combination with one or more other compounds of the invention or in combination with one or more other drugs (or as any combination thereof. For example, the compounds of the present invention may be administered in combination with an oral contraceptive. Alternatively, they may be administered in combination with a PDE5 inhibitor. They may also be administered in combination with an NO donor. Alternatively, they may be administered in combination with L-arginine, or as an arginate salt. The compounds of the present invention may also be used in combination with a COX inhibitor.

Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Thus, according to another aspect of the present invention, there is provided a pharmaceutical formulation comprising a compound of formula (I) in admixture with a pharmaceutically acceptable adjuvant, diluent or carrier.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example water, ethanol, polyethylene glycol, propylene glycol, methylcellulose, or a suitable oil, and one or more emulsifying agents and/or suspending agents. Liquid formulations may also be prepared by the reconstitution of a solid, for example from a sachet.

The compounds of the invention may also be used in fast-dissolving, fast disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt %, of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatnised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, anid glidants may comprise from 0.2 wt % and 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt %, of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms, Tablets, Vol. 1", by H. Liebernan and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted- and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intreperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled-, targeted- and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example. J. Pharm. Sci., 88 (10), 955-958 by Finnin and Morgan (October 1999).

Other means of topical administration include delivery by iontophoresis, electroporation, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer or nebuliser contains a solution or suspension of the compound(s) of the invention comprising, for example, ethanol, aqueous ethanol, or a suitable alternative agent for dispersing, solubilising or extending release of the active, the propellant(s) as solvent and an optional surfactant, such as sorbitan trioleate, oleic acid, or an oligolactic acid.

Prior to use in a dry powder of suspension formulation, the drug product is micronised to a size suitable for delivery by inhalation (typically less than 5 microns). This may be achieved by any appropriate comminuting method, such a spiral jet milling, fluid bed jet milling, supercritical fluid processing to form nanoparticles, high pressure homogenisation or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose arid trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly-DL-lactic-coglycolic acid (PGLA). Modified release formulations include delayed-, sustained-, pulsed-, controlled-, targeted and programmed release.

The compounds of the invention may be administered rectally or vaginally, for example, in the form of a suppository, pessary or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic, acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities such as cyclodextrin or polyethylene glycol-containing polymers to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent or solubiliser. Most commonly used for these purposes are alpha-, beta- and gamma-cyclodextrins, examples of which may be found in International Patent Applications Nos. WO 91/11172. WO 94/02518 and WO 98/55148.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compounds of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention will typically be in the range of from about 0.01 to about 15 mg/kg of body weight, depending on the mode of administration. The total daily dose may be administered in a single dose or divided doses throughout the day. These dosages are based on an average human subject having a weight of about 65 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or stow the appearance of symptoms. The term "treatment" includes alleviation, elimination of causation (either on a temporary or permanent basis) of, or prevention of symptoms and disorders associated with primary and/or secondary dysmenorrhoea. The treatment may be a pre-treatment as well as a treatment at the on-set of symptoms.

The compounds of the present invention may be tested in the screens set out below:

1.0 $V_{1A}$ Filter Binding Assay 1.1 Membrane Preparation

Receptor binding assays were performed on cellular membranes prepared from CHO cells stably expressing the human $V_{1A}$ receptor, (CHO-h$V_{1A}$). The CHO-h$V_{1A}$ cell line was kindly provided under a licensing agreement by Marc Thibonnier, Dept. of Medicine, Case Western Reserve University School of Medicine, Cleveland, Ohio, CHO-h$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. For bulk production of cell pellets, adherent CHO-h$V_{1A}$ cells were grown to confluency of 90-100% in 850 $cm^2$ roller bottles containing a medium of DMEM/Hams F12 Nutrient Mix supplemented with 10% fetal bovine serum, 2 mM L-gitidtamine and 15 mM HEPES. Confluent CHO-h$V_{1A}$ cells were washed with phosphate-buffered saline (PBS), harvested into ice cold PBS and centrifuged at 1,000 rpm. Cell pellets were stored at −80° C. until use. Cell pellets were thawed on ice and homogenised in membrane preparation buffer consisting of 50 mM Tris-HCl, pH 7.4, 5 mM $MgCl_2$ and supplemented with a protease inhibitor cocktail, (Roche). The cell homogenate was centrifuged at 1000 rpm, 10 min, 4° C. and the supernatant was removed and stored on ice. The remaining pellet was homogenised and centrifuged as before. The supernatants were pooled and centrifuged at 25,000×g for 30 min at 4° C. The pellet was resuspended in freezing buffer consisting of 50 mM Tris-HCl, pH 7.4, 5 mM $MgCl_2$ and 20% glycerol and stored in small aliquots at −80° C. until use. Protein concentration was determined using Bradford reagent and BSA as a standard.

1.2 $V_{1A}$ Filter Binding

Protein linearity followed by saturation binding studies were performed on each new batch of membrane. Membrane concentration was chosen that gave specific binding on the linear portion of the curve. Saturation binding studies were then performed using various concentrations of [$^3$H]-arginine vasopressin, [$^3$]-AVP (0.05 nM-100 nM) and the Kd and Bmax determined.

Compounds were tested for their effects on [$^3$H]-AVP binding to CHO-h$V_{1A}$ membranes, ($^3$H-AVP; specific activity 65.5 Ci/mmol: NEN Life Sciences). Compounds were solubilised in dimethylsulfoxide (DMSO) and diluted to working concentration of 10% DMSO with assay buffer containing 50 mM Tris-HCL pH 7.4, 5 mM $MgCl_2$ and 0.05% BSA, 25 µl compound and 25 µl [$^3$H]-AVP, (final concentration at or below $K_d$ determined for membrane batch, typically 0.5 nM-0.6 nM) were added to a 96-well round bottom polypropylene plate. The binding reaction was initiated by the addition of 200 µl membrane and the plates were gently shaken for 60 min at room temperature. The reaction was terminated by rapid filtration using a Filtermate Cell Harvester (Packard Instruments) through a 96-well GF/B UniFilter Plate which had been presoaked in 0.5% polyethiylene-iminie to prevent peptide sticking. The filters were washed three times with 1 ml ice cold wash buffer containing 50 mM Tris-HCL pH 7.4 and 5 mM $MgCl_2$. The plates were dried and 50 µl Microscint-0 (Packard instruments) was added to each well. The plates were sealed and counted on a TopCount Microplate Scintillation Counter (Packard Instruments). Non-specific binding (NSB) was determined using 1 µM unlabelled d(CH2)5Tyr(Me)AVP ([β-mercapto-β,β-cyclopentamethylenepropionyl,0-Me-Tyr$^2$,Arg$^8$]-vasopressin) (βMCPVP), (Sigma). The radioligand binding data was analysed using a four parameter logistic equation with the min forced to 0%. The slope was free fitted and fell between −0.75 and −1.25 for valid curves. Specific binding was calculated by subtracting the mean NSB cpm from the mean Total cpm. For test compounds the amount of ligand bound to the receptor was expressed as % bound=(sample cpm−mean NSB cpm)/specific binding cpm×100. The % bound was plotted against the concentration of test compound and a sigmoidal curve was fitted. The inhibitory dissociation constant (Ki) was calculated using the Cheng-Prusoff equation: $Ki=IC_{50}/(1+[L]/K_d)$ where [L] is the concentration of ligand present in the well and $K_d$ is the dissociation constant of the radioligand obtained from Scatchard plot analysis.

2.0 $V_{1A}$ Functional Assay; Inhibition of AVP/$V_{1A}$-R mediated $Ca^{2+}$ Mobilization by FLIPR (Fluorescent Imaging Plate Reader) (Molecular Devices)

Intracellular calcium release was measured in CHO-h$V_{1A}$ cells using FLIPR, which allows the rapid detection of calcium following receptor activation. The CHO-h$V_{1A}$ cell line was kindly provided under a licensing agreement by Marc Thibonnier, Dept. of Medicine, Case Western Reserve University School of Medicine, Cleveland, Ohio. CHO-$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. On the afternoon before the assay cells were plated at a density of 20,000 cells per well into black sterile 96-well plates with clear bottoms to allow cell inspection and fluorescence measurements from the bottom of each well. Wash buffer containing Dulbecco's phosphate buffered saline (DPBS) and 2.5 mM probenecid and loading dye consisting of cell culture medium containing 4 µM Fluo-3-AM (dissolved in DMSO and pluronic acid),(Molecular Probes) and 2.5 mM probenecid was prepared fresh on the day of assay. Compounds were solubilised in DMSO and diluted in assay buffer consisting of DPBS containing 1% DMSO, 0.1% BSA and 2.5 mM probenecid. The cells were incubated with 100 µl loading dye per well for 1 hour at 37° C. in humidfiefd atmosphere with 5% $CO_2$. After dye loading the cells were washed three times in 100 µl wash buffer using a Denley plate washer. 100 µl wash buffer was left in each well. Intracellular fluorescence was measured using FLIPR. Fluorescence readings were obtained at 2 s intervals with 50 µl of the test compound added after 30 s. An additional 155 measurements at 2 s intervals were then taken to detect any compound agonistic activity. 50 µl of arginine vasopressin (AVP) was then added so that the final assay volume was 200 µl. Further fluorescence readings were collected at 1 s intervals for 120 s. Responses were measured as peak fluorescence intensity (FI). For pharmacological characterization a basal FI was subtracted from each fluorescence response. For AVP dose response curves, each response was expressed as a % of the response to the highest concentration of AVP in that row. For $IC_{50}$ determinations, each response was expressed as a % of the response to AVP. IC50 values were converted to a modified $K_b$ value using the Cheng-Prusoff equation which takes into account the agonist concentration, [A], the agonist $EC_{50}$ and the slope: $K_b=IC_{50}/(2+[A]/A_{50})^n)^{1/n}-1$ where [A] is the concentration of AVP, $A_{50}$ is the $EC_{50}$ of AVP from the dose response curve and n=slope of the AVP dose response curve.

The compounds of the invention may have the advantage that they are more potent, have a longer duration of action, have a broader range of activity, are more stable, have fewer side effects or are more selective, or have other more useful properties than the compounds of the prior art.

Thus the invention provides:
(i) a compound of formula (I) or a pharmaceutically acceptable derivative thereof;
(ii) a process for the preparation of a compound of formula (I) or a pharmaceutically acceptable derivative thereof;
(iii) a pharmaceutical formulation including a compound of formula (I) or a pharmaceutically acceptable derivative thereof, together with a pharmaceutically acceptable excipients, diluent or carrier;
(iv) a compound of formula (I) or a pharmaceutically acceptable derivative or composition thereof, for use as a medicament;
(v) the use of a compound of formula (I) or of a pharmaceutically acceptable derivative or composition thereof, for the manufacture of a medicament for the treatment of aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis;
(vi) use as in (v) where the disease or disorder is anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease;
(vii) use as in (v) where the disease or disorder is dysmenorrhoea (primary and secondary);
(viii) a method of treatment of a mammal to treat aggression, Alzheimer's disease, anorexia nervosa, anxiety, anxiety disorder, asthma, atherosclerosis, autism, cardiovascular disease (including angina, atherosclerosis, hypertension, heart failure, edema, hypernatremia), cataract, central nervous system disease, cerebrovascular ischemia, cirrhosis, cognitive disorder, Cushing's disease, depression, diabetes mellitus, dysmenorrhoea (primary and secondary), emesis (including motion sickness), endometriosis, gastrointestinal disease, glaucoma, gynaecological disease, heart disease, intrauterine growth retardation, inflammation (including rheumatoid arthritis), ischemia, ischemic heart disease, lung tumor, micturition disorder, mittlesmerchz, neoplasm, nephrotoxicity, non-insulin dependent diabetes, obesity, obsessive/compulsive disorder, ocular hypertension, preclampsia, premature ejaculation, premature (preterm) labor, pulmonary disease, Raynaud's disease, renal disease, renal failure, male or female sexual dysfunction, septic shock, sleep disorder, spinal cord injury, thrombosis, urogenital tract infection or urolithiasis including treating said mammal with an effective amount of a compound of formula (I) or with a pharmaceutically acceptable derivative or composition thereof;
(ix) a method as in (vii) where the disease or disorder is anxiety, cardiovascular disease (including angina, atherosclerosis, hypertension, heart failure, edema, hypernatremia), dysmenorrhoea (primary and secondary), endometriosis, emesis (including motion sickness), intrauterine growth retardation, inflammation (including rheumatoid arthritis), mittlesmerchz, preclampsia, premature ejaculation, premature (preterm) labor or Raynaud's disease;
(x) a method as in (vii) where the disease or disorder is dysmenorrhoea (primary and secondary);
(xi) use of a combination of a compound of formula (I) with an oral contraceptive for treating dysmenorrhoea (primary and/for secondary);
(xii) use of a combination of a compound of formula (I) with a PDE5 inhibitor for treating dysmenorrhoea (primary and/or secondary);
(xiii) use of a combination of a compound of formula (I) with an NO donor for treating dysmenorrhoea (primary and/or secondary);
(xiv) use of a combination of a compound of formula (I) with L-arginine for treating dysmenorrhoea (primary and/or secondary);
(xv) use of a combination of a compound of formula (I) with a COX inhibitor for treating dysmenorrhoea (primary and/or secondary).

The invention is illustrated by the following preparations and examples:

Preparation 1: tert-Butyl
4-pyridin-2-ylpiperidine-1-carboxylate

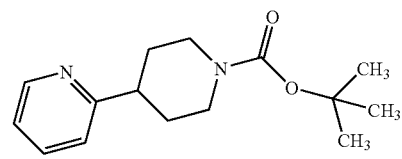

Zinc powder (10.50 g, 160.60 mmol) was added to 2M hydrochloric acid (25 mL) and the resulting suspension was stirred for 20 minutes. It was then filtered and washed with water (10 mL), ethanol (10 mL), diethyl ether (10 mL) and dried in a vacuum oven for 24 hours. The dried zinc was suspended in N,N-dimethylformamide (50 mL) and 1,2-dibromoethane (277 μL, 3.21 mmol) was added. The resulting suspension was warmed to 65° C. for 5 minutes and then allowed to cool to room temperature, after which time trimethylsilyl chloride (406 μL, 3.2 mmol) was added. The reaction was stirred at room temperature for 45 minutes and then a solution of tert-butyl 4-iodopiperidine-1-carboxylate (Synlett, 4, 379, 1998) (10 g, 32.1 mmol) and hydroquinone (177 mg, 0.05 mmol) in N,N-dimethylformamide (50 mL) was slowly added, followed by warming to 150° C. for 30 minutes. 2-bromopyridine (3.06 mL, 32.10 mmol) in N,N-dimethylformamide (20 mL) was then added, followed by 5 mol % of $Pd_2(dba)_3$ (1.44 g, 1.57 mmol), 10 mol % P-(2-furyl)$_3$ (747 mg, 3.22 mmol) and the reaction was heated at 65° C. for 24 hours. The reaction mixture was filtered through Celite® and diluted with water (500 mL). It was then extracted with diethyl ether (2×250 ml). The organic layers were combined and washed with brine, dried over magnesium sulfate and concentrated in vacuo to give the crude residue. Purification by column chromatography on silica gel using diethyl ether: pentane (50:50-100:0) as eluent afforded the product as a yellow oil, 1.9 g (23%).

1H NMR (400 MHz, $CDCl_3$): δ 1.45 (9H, s), 1.72 (2H, m), 1.93 (2H, m), 2.70-2.95 (3H, m), 4.26 (2H, m), 7.07-7.20 (2H, m), 7.63 (1H, m), 8.54 (1H, dd).

Preparation 2: 2-Piperidin-4-ylpyridine

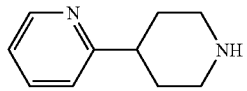

To a stirred solution of the compound from preparation 1 (2.04 g, 7.79 mmol) in dioxane (20 mL) was added 4M HCl/dioxane solution (10 mL) and the reaction was left to stir for 27 hours at room temperature. Methanol (10 ml) was then added followed by 4M HCl/dioxane solution (5 mL) and the reaction stirred for a further 3 hours. The solvent was removed in vacuo and the resulting yellow powder was triturated with ethyl acetate. The residue was then suspended in dichloromethane (10 mL) and dilute ammonia solution was added. The phases were separated and the aqueous phase was extracted with dichloromethane. The combined organic extracts were washed with brine, dried over magnesium sulfate and concentrated in vacuo to afford the title product as a maroon oil, 1.27 g (100%).

$^1$H NMR (400 MHz, $CDCl_3$): δ 1.70-1.80 (2H, m)), 1.90-2.00 (2H, m), 2.78-2.90 (3H, m), 3.20-3.50 (2H, m), 7.10-7.30 (2H, m), 7.60 (1 H, m), 8.50 (1H, m).
LRMS: m/z APCl+163 [MH$^+$].

Preparation 3: 2-({[tert-Butyl(dimethyl)silyl]oxy}methyl)-4-chloroaniline

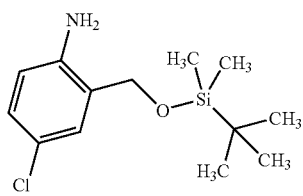

To a stirred solution of 2-amino-5-chlorophenylmethanol (11.1 g, 70.4 mmol) in tetrahydrofuran (50 mL) was added imidazole (5.27 g, 77.5 mmol), followed by careful addition of tert-butyldimethylchlorosilane (10.62 g 70.4 mmol). The reaction mixture was stirred for 24 hours. Imidazole (528 mg, 7.75 mmol) and tert-butyldimethylchlorosilane (1.06 g, 7.03 mmol) were then added. After 1 hour the solid was filtered off and washed with diethyl ether (2×20 mL) and the filtrate was washed with water (10 mL), brine (10 mL), dried over magnesium sulfate and concentrated in vacuo to give the product as a brown oil, 18.83 g (98%).

$^1$ H NMR (400 MHz, $CDCl_3$): δ 0.07 (6H, s), 0.90 (9H, s), 4.63 (2H, s), 6.60 (1H, d), 7.01 (1H, d), 7.05 (1H, m); LRMS: m/z APCl+272[MH$^+$].

Preparation 4: tert-Butyl[(5-chloro-2-isothiocyanatobenzyl)oxy]dimethylsilane

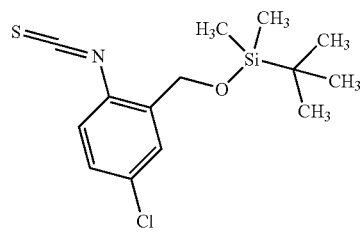

To a solution of aniline from preparation 3 (85.9 g, 316 mmol) in dichloromethane (500 mL) was added triethylamine (76.5 mL, 549 mmol) and the whole solution was cooled to −6° C. Thiophosgene (23.3 mL, 305.8 mmol) was then added dropwise over 2.5 hours. After the addition was complete, the solution was washed with water (450 mL), then with brine (100 mL). The organic phase was dried over magnesium sulfate and concentrated in vacuo to give the crude residue. Purification by column chromatography on silica gel, using pentane as eluent, afforded the product as a yellow oil, 81.9 g (83%).

$^1$H NMR (400 MHz, $CDCl_3$): δ 0.14 (6H, s), 0.95 (9H, s), 4.74 (2H, s), 7.13 (1H, d), 7.21 (1H, dd), 7.48 (1H, d); LRMS: m/z APCl+314[MH$^+$].

Preparation 5: N-[2-({[tert-Butyl(dimethyl)silyl]oxy}methyl)-4-chlorophenyl]-4-pyridin-2-ylpiperidine-1-carbothioamide

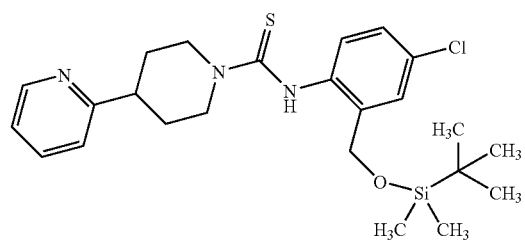

To a stirred solution of the compound from preparation 2 (1.39 g, 8.57 mmol) in ethanol (30 mL) was added the compound from preparation 4 (2.69 g, 8.57 mmol) and the reaction mixture was stirred for 66 hours. The solvent was removed in vacuo to give the crude residue, which was purified by column chromatography on silica gel using dichloromethane and then ethyl acetate as eluent to afford the desired product, 3.35 g (82%).

¹H NMR (400 MHz, CDCl₃): δ 0.07 (6H s), 0.88 (9H, s), 1.93 (2H, m), 2.08 (2H, m), 3.06 (1H, m), 3.24 (2H, m), 4.64 (2H, s), 4.88 (2H, m), 7.10-7.21 (3H, m), 7.29 (1H, dd), 7.66 (1H, dd), 7.82 (1H, d), 8.42 (1H, s) 8.66 (1H, d); LRMS: m/z APCl+476 [MH⁺].

Preparation 6: N-[2-({[tert-Butyl(dimethyl)silyl]oxy}methyl)-4-chlorophenyl]-4-pyridin-2-ylpiperidine-1-carbimidothioic acid

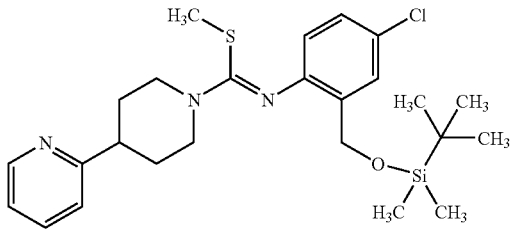

To a solution of the compound from preparation 5 (3.32 g 6.9 7mmol) in tetrahydrofuran (20 mL) was added potassium tert-butoxide (862 mg, 7.68 mmol). After 10 minutes methyl p-toluene sulfonate (1.30 g, 6.97 mmol) was added. After a further 10 minutes TLC analysis showed that starting material remained, so additional methyl p-toluenesulfonate (119 mg, 0.64 mmol) was added and the reaction stirred for a further 5 minutes. The solvent was removed in vacuo and the residue partitioned between dichloromethane (50 ml) and water (50 ml). The organic layer was separated, the solvent removed in vacuo and the residue azeotroped with dichloromethane to afford the product as an oil in quantitative yield.

¹H NMR (400 MHz, CDCl₃) δ 0.08 (6H, s), 0.94 (9H, s) 1.86 (2H, m), 2.00 (2H, m), 2.06 (3H, s) 2.95 (1H, m), 3.05 (2H, m), 4.40 (2H, m), 4.58 (2H, s), 6.72 (1H, d), 7.09 (1H, dd), 7.14 (1H, m), 7.17 (1H, d), 7.41 (1H, d), 7.64 (1H, m), 8.55 (1H, d), LRMS: m/z APCl+490 [MH⁺].

Preparation 7: tert-Butyl 2-hydrazino-2-oxoethylcarbamate

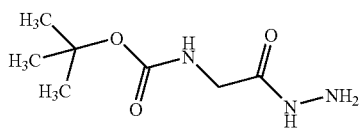

To a stirred solution of methyl (tert-butyloxycarbonyl)glycinate (8.54 g, 45.1 mmol) was added hydrazine hydrate (4.4 mL, 90.5 mmol) and the reaction was heated under reflux for 16 hours. The solvent was removed in vacuo and the residue partitioned between dichloromethane (100 mL) and water (100 mL). The phases were separated, the aqueous phase evaporated in vacuo to low volume and extracted with 5% methanol/dichloromethane (2×100 mL) The organic extracts were combined, dried over magnesium sulfate and concentrated in vacuo to give the product as a white crystalline solid, 5.27 g (62%).

¹H NMR (400 MHz, CDCl₃) δ 1.44 (9H, s), 3.80 (2H, d), 5.11 (1H, bs).

Preparation 8: tert-Butyl {[4-[2-({[tert-butyl(dimethyl)silyl]oxy}methyl)-4-chlorophenyl]-5-(4-pyridin-2-ylpiperidin-1-yl)-4H-1,2,4-triazol-3-yl]methyl}carbamate

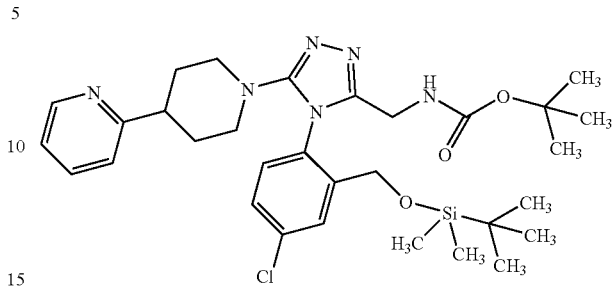

To a stirred solution of the compound from preparation 6 (3.42 g, 6.97 mmol) in tetrahydrofuran (10 mL) was added the compound of preparation 7 (2.62 g, 14.0 mmol) followed by trifluoroacetic acid (0.28 mL, 3.63 mmol) and the solution was refluxed for 24 hours. The reaction was basified with dilute ammonia solution (20 mL) and then dichloromethane (50 mL) was added. The phases were separated. The organic phases were washed with brine, dried over magnesium sulfate and concentrated in vacuo. The crude residue was purified by column chromatography on silica gel using ethyl acetate then dichloromethane:methanol (95.5) as eluent to afford the desired product as a white foam, 1.44 g (34%).

¹H NMR (400 MHz, CDCl₃): δ 0.06 (6H, 2×s), 0.89 (9H, s), 1.34 (9H, s), 1.72 (2H, m), 1.80 (1H, m), 1.96 (1H, m), 2.74-2.87 (2H, m), 3.09 (1H, m), 2.36 (1H, m), 2.55 (1H, m), 4.18 (2H, d), 4.38 (1H, d), 4.55 (1H, d), 5.20 (1H, m), 7.10-7.15 (2H, m), 7.18 (1H, d), 7.40 (1H, m), 7.58-7.65 (2H, m), 8.51 (1H, d); LRMS: m/z APCl+613[MH⁺].

Preparation 9: tert-Butyl {[4-[4-chloro-2-(hydroxymethyl)phenyl]-5-(4-pyridin-2-ylpiperidin-1-yl)-4H-1,2,4-triazol-3-yl]methyl}carbamate

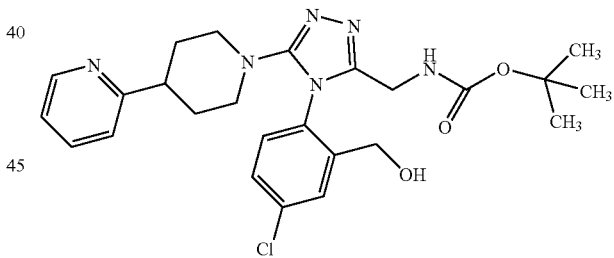

To an ice-cooled solution of the compound from preparation 8 (1.42 g, 2.32) in tetrahydrofuran (50 mL) was added tetra-n-butylammonium fluoride (646 mg, 2.31 mmol). After 40 minutes a solution of saturated sodium hydrogen carbonate (20 mL) was added and the reaction stirred for a further 30 minutes. The phases were separated and the organic phase was washed with brine (20 mL), dried over magnesium sulfate and concentrated in vacuo to give the crude residue. Purification by column chromatography on silica gel using dichloromethane:methanol:0.88 ammonia (90:10:1) afforded the desired product, 929 mg (80%).

¹H NMR (400 MHz, CDCl₃): δ 1.24 (9H, s), 1.47-1.60 (1H, m), 1.61-1.74 (2H, m), 1.78-1.87 (1H, m) 2.64-2.75 (2H, m), 2.93-3.04 (1H, m), 3.19 (1H, m), 3.48 (1H, m), 4.10 (2H, m), 4.28 (1H, d), 4.36 (1H, d), 5.70 (1H, n), 7.00-7.05 (2H, m), 7.11 (1H, d), 7.33 (1H, dd), 7.52 (1H, m), 7.63 (1H, m), 8.39 (1H, m).

LRMS: m/z APCl+499[MH⁺].

Preparation 10: 2-[3-{[(tert-Butoxycarbonyl)amino]methyl}-5-(4-pyridin-2-ylpiperidin-1-yl)-4H-1,2,4-triazol-4-yl]-5-chlorobenzyl methanesulfonate

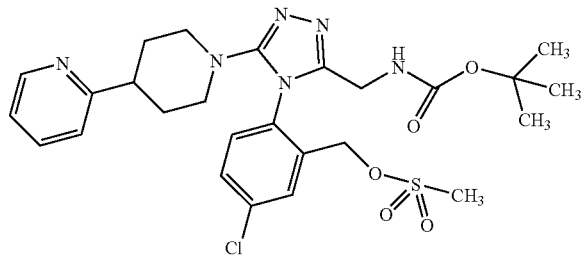

To a stirred Solution of the compound from preparation 9 (1.89 g, 3.79 mmol) in dichloromethane (50 mL) at 0° C. was added triethylamine (792 µL, 5.68 mmol) followed by methanesulfonyl chloride (352 µL, 4.54 mmol). After 30 minutes of stirring, second portions of triethylamine (792 µL, 5.68 mmol) and methane sulfonyl chloride (352 µ, 4.54 mmol) were added. After a further 15 minutes the reaction was washed with water (20 mL), brine (20 mL) and dried over magnesium sulfate. The solution was concentrated in vacuo gave the crude residue which was purified by column chromatography on silica gel using dichloromethane:methanol (95:5) as eluent to give the product as a white foam, 660 mg (30%).

$^1$H NMR (400 MHz, CDCl$_3$): δ 1.34 (9H, S), 1.65 (1H, m), 1.72-1.87 (2H, m), 1.96 (1H, bd), 2.74-2.86 (2H, m), 2.99 (3H, s), 3.14 (1H, m), 3.23 (1H, bd), 3.61 (1H, bd), 4.21 (2H, d), 5.00 (1H, d), 5.12 (1H, d), 5.24 (1H, m): 7.10-7.17 (2H, m), 7.32 (1H, d), 7.53 (1H, dd), 7.60-7.67 (2H, m), 8.52 (1H, d); LRMS: m/z APCl+577[MH$^+$].

Preparation 11: Ethyl N-(tert-butoxycarbonyl)-N-methylglycinate

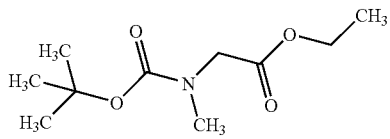

To a stirred solution of ethyl N-methylglycinate (10 g, 65.1 mmol) in dichloromethane (100 mL) was added triethylamine (9.1 mL, 65.3 mmol) (which caused a white precipitate to form). The solid was filtered, di-tert-butyl dicarbonate (14.08 g, 64.5 mmol) added to the filtrate and the reaction mixture was stirred for 66 hours. The reaction was then washed with water (2×100 mL), brine (5 mL) and dried over magnesium sulfate. Concentration in vacuo gave the product as an oil, 14.51 g (100%).

$^1$R NMR (400 MHz, CDCl$_3$): δ 1.27 (3H, 2×t) 1.44 (9H, 2×s) 2.92 (3H, 2×s) 3.91 (2H, d), 4.18 (2H, m); LRMS: m/z APCl+218[MH$^+$].

Preparation 12: Hydrazinocarbonylmethyl-methyl-carbamic acid tert-butyl ester

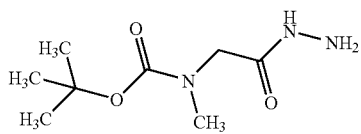

To a stirred solution of the compound from preparation 11 (14.5 g, 65.1 mmol) in ethanol (100 mL) was added hydrazine hydrate (3.20 mL, 65.2 mmol) and the mixture was heated under reflux for 24 hours. After this time a second portion of hydrazine hydrate (3.20 mL, 65.2 mmol) was added and the reaction heated tinder reflux for a further 24 hours. The solvent was evaporated in vacuo to give the crude residue. This was partitioned between diethyl ether and water. The phases were separated and the aqueous phase was extracted with dichloromethane. The organic extracts were combined, dried over magnesium sulfate and concentrated in vacuo to give the product as a white solid, 10.44 g (79%).

$^1$H NMR (400 MHz, CDCl$_3$): δ 1.45 (9H, s), 2.93 (3H, s), 3.20 (2H, bs), 3.87 (2H, s);

Preparation 13: N-[2-({[tert-butyl(dimethyl)silyl]oxy}methyl)-4-chlorophenyl]-4-phenylpiperidine-1-carbothioamide

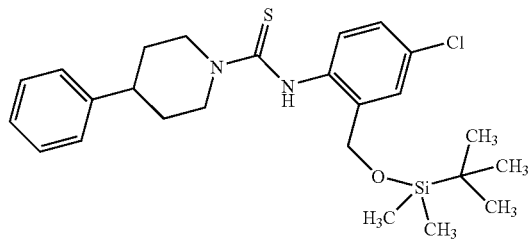

To a solution of the compound from preparation 4 (2 g, 6.37 mmol) in diethyl ether was added 4-phenylpiperidine (957 mg, 6.37 mmol) and the mixture was stirred for 66 hours, 4-phenyl piperidine (63 mg, 0.42 mmol) was added and the reaction was stirred for a further 30 minutes. The solvent was removed in vacuo and the residue azeotroped with dichloromethane to give the product as a foam, 2.91 g (98%).

$^1$H NMR (400 MHz, CDCl$_3$): δ 0.08 (6H, s), 0.88 (9H, s) 1.82 (2H, m), 1.96 (2H, m), 2.84 (1H, m), 3.17 (2H, m), 4.66 (2H, s), 4.89 (2H, m), 7.17 (1H, d), 7.19-7.38 (6H, m), 7.83 (1H, d), 8.40 (1H, bs); LRMS: m/z APCl+475[MH$^+$].

Preparation 14: N-[2-({[tert-Butyl(dimethyl)silyl]oxy}methyl)-4-chlorophenyl]-4-phenylpiperidine-1-carbimidothioic acid

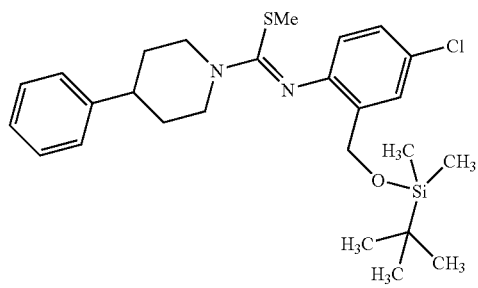

To a stirring solution of the compound from preparation 13 (2.88 g, 6.06 mmol) in tetrahydrofuran (40 mL) was added potassium tert-butoxide (692 mg, 6.17 mmol). After 10 minutes methyl p-toluenesulfonate (1.15 g, 6.2 mmol) was added and the resulting mixture was stirred for a further 24 hours. The solvent was removed in vacuo and the residue partitioned between dichloromethane (50 mL) and water (50 mL). The organic phase was washed with brine (25 mL), dried over magnesium sulfate and concentrated in vacuo to the crude residue. Purification by column chromatography on silica gel using pentane:ethyl acetate (95:5) as eluent afforded the pure product as an oil, 2.87 g (97%).

$^1$H NMR (400 MHz, CDCl$_3$) δ 0.12 (6H, s), 0.94 (9H, s), 1.75 (2H, m), 1.92 (2H, m), 2.07 (3H, s), 2.77 (1H, m), 3.01 (2H, m), 4.40 (2H, m), 4.60 (2H, s), 6.74 (1H, d), 7.11 (1H, m), 7.11 (1H, dd), 7.20-7.25 (3H, m), 7.30-7.35 (2H, m), 7.42 (1H, d); LRMS: m/z APCl+489[MH⁺].

Preparation 15: tert-Butyl {[4-[2-({[tert-butyl(dimethyl)silyl]oxy}methyl)-4-chlorophenyl]-5-(4-phenylpiperidin-1-yl)-4H-1,2,4-triazol-3-yl]methyl}methylcarbamate

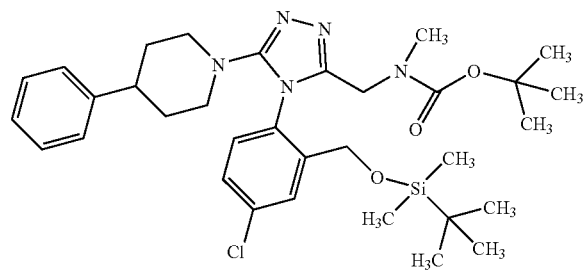

To a stirred solution of the compound from preparation 14 (2.75 g, 5.62 mmol) and compound from preparation 12 (1.16 g, 5.72 mmol) in n-butyl alcohol (20 mL) was added acetic acid (0.5 mL, 8.73 mmol) and the reaction mixture was heated at 120° C. for 14 hours. More hydrazide (558 mg, 2.74 mmol) was then added. After a further 1.5 hours the reaction was cooled and the solvent was removed in vacuo to give the crude residue. Purification by column chromatography on silica gel using ethyl acetate then dichloromethane:methanol (95:5) gave the product as a yellow oil, 2.23 g (63%).

$^1$H NMR (400 MHz, CDCl$_3$) δ 0.08 (6H, s), 0.93 (9H, s), 1.17-1.33 (9H, s), 1.46-1.88 (4H, m), 2.59 (1H, m), 2.76 (3H, s), 2.81 (1H, m), 3.06 (1H, m), 3.34 (1H, m), 3.55 (1H, m), 4.25 (2H, d), 4.60 (2H, m), 7.07-7.15 (3H, m), 7.19 (1H, d), 7.30 (2H, m), 7.36 (1H, dd), 7.67 (1H, bs).

Preparation 16: tert-butyl {[4-[4-chloro-2-(hydroxymethyl)phenyl]-5-(4-phenylpiperidin-1-yl)-4H-1,2,4-triazol-3-yl]methyl}methylcarbamate

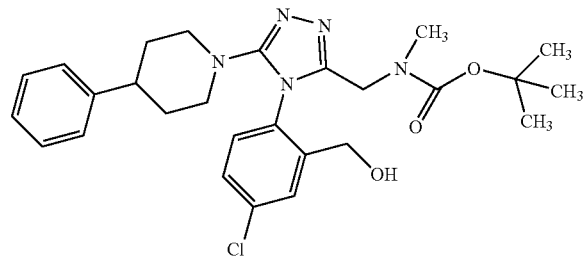

To a stirred solution of the compound from preparation 15 (2.23 g, 3.50 mmol) in tetrahydrofuran (50 mL) at 0° C. was added tetra-n-butylammonium fluoride trihydrate (1.14 g, 3.60 mmol) and the reaction was stirred for 2 hours at 0° C. The reaction was diluted with saturated sodium hydrogen carbonate solution (20 mL) and stirring continued for 10 minutes. The phases were separated and the aqueous phase was extracted using ethyl acetate. The organic extracts were combined dried over magnesium sulfate and concentrated in vacuo to give the crude residue. Purification by column chromatography on silica gel using dichloromethane:methanol (95:5) as eluent gave the product as a white foam, 1.17 g (64%).

$^1$H NMR (400 MHz, CDCl$_3$): δ 1.31 (9H, s), 1.48-1.92 (4H, m), 2.60 (1H, m), 2.68-2.90 (4H, m), 3.05 (1H, m), 3.33 (1H, m), 3.48 (1H, m), 4.32 (2H, s), 4.42 (2H, m), 7.08-7.18 (3H, m), 7.20 (1H, d), 7.26 (2H, m), 7.41 (1H, m), 7.71 (1H, d).

Preparation 17: 2-[3-{[(tert-Butoxycarbonyl)(methyl)amino]methyl}-5-(4-phenylpiperidin-1-yl)-4H-1,2,4-triazol-4-yl]-5-chlorobenzyl methanesulfonate

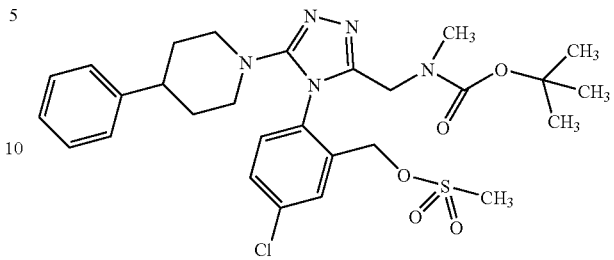

To a stirred solution of the compound from preparation 16 (1.15 g, 2.25 mmol) in dichloromethane (50 mL) was added triethylamine (376 μl, 2.70 mmol). The solution was cooled to 0° C. and methanesulfonyl chloride (174 μl, 2.25 mmol) was added and the reaction stirred for 1.5 hours. The reaction was then warmed to 20° C. and triethylamine (376 μl, 2.70 mmol) and methanesulfonyl chloride (174 μl, 2.25 mmol) were added. After a further 1.5 hours the reaction was washed with water (2×20 ml) then with brine (20 ml), dried over magnesium sulfate and concentrated in vacuo. Purification by column chromatography on silica gel using dichloromethane:methanol (95:5) as eluent gave the product as a white foam 911 mg (69%).

$^1$H NMR (400 MHz, CDCl$_3$): δ 1.26 (9H, s), 1.65 (2H, m), 1.78-2.00 (2H, m), 2.56 (1H, m), 2.71-2.86 (4H, m), 2.95 (3H, s), 3.06 (1H, m), 3.28 (1H, m), 3.54 (1H, m) 4.25-4.45 (2H, m), 4.96 (1H, d), 5.12 (1H, d), 7.13 (3H, m), 7.18 (1H, d), 7.25 (2H, m), 7.48 (1H, d), 7.62 (1H, s).

Preparation 18 & Preparation 19: tert-Butyl {[4-[2-({[tert-butyl(dimethyl)silyl]oxy}methyl)-4-chlorophenyl]-5-(4-phenylpiperidin-1-yl)-4H-1,2,4-triazol-3-yl]methyl}carbamate

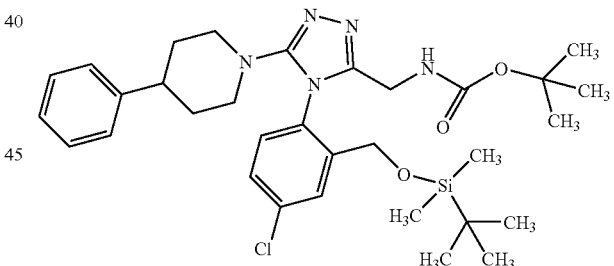

tert-Butyl {[4-[4-chloro-2-(hydroxymethyl)phenyl]-5-(4-phenylpiperidin-1-yl)-4H-1,2,4-triazol-3-yl]methyl}carbamate

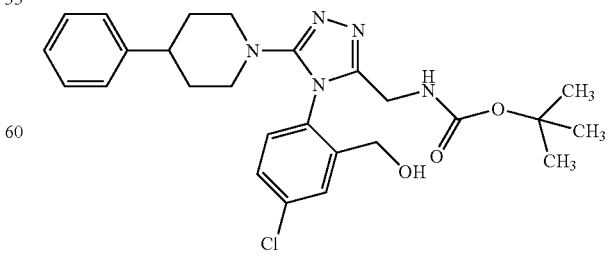

To a stirred solution of the compound from preparation 14 (6.4 g, 13.08 mmol) in tetrahydrofuran (100 mL) was added the compound from preparation 7 (4.58 g, 24.2 mmol) and trifluoroacetic acid (1 mL, 12.98 mmol). The reaction mixture was heated under reflux for 16 hours. The reaction was then cooled to 20° C. and a solution of 0.88 ammonia (20 mL) was added and the mixture stirred vigorously. The phases were separated and the aqueous phase was extracted with dichloromethane (100 mL). The organic extracts were combined, dried over sodium sulfate and concentrated in vacuo to give the crude residue. Purification by column chromatography on silica gel using ethyl acetate and then dichloromethane:methanol (95:5) to afforded the desired product of preparation 18, 2.70 g (34%).

$^1$H NMR (400 MHz: CDCl$_3$): δ 0.07 (6H, 2×s), 0.93 (9H, s), 1.38 (9H, s), 1.58-1.85 (4H, m), 2.60 (1H, m), 2.81 (1H, m), 3.07 (1H, m), 3.32 (1H, m), 3.58 (1H, m), 4.08 (2H, m), 4.38 (1H, d), 4.66 (1H, d), 5.18 (1H, bs), 7.10-7.20 (4H, m), 7.25 (2H, m), 7.40 (1H, m), 7.63 (1H, s); LRMS: m/z APCl+ 613[MH$^+$].

Further elution yielded the compound of preparation 19, 2.7 g (34%).

$^1$H NMR (400 MHz, CDCl$_3$) δ 1.33 (9H, s), 1.52 (1H, m), 1.63 (1H, m), 1.68 (1H, m), 1.87 (1H, m), 2.58 (1H, n), 2.79 (1H, m), 3.07 (1H, m), 3.17 (1H, m), 3.55 (1H, m), 3.91 (2H, d), 4.39 (2H, s) 5.54 (1H, m), 5.69 (1H, m), 7.13 (2H, m), 7.20 (1H, d). 7.25 (3H, m), 7.44 (1H, dd), 7.71 (1H, d), LRMS: m/z APCl+498[MH$^+$].

Preparation 20: 2-[3-{[(tert-Butoxycarbonyl)amino]methyl}-5-(4-phenylpiperidin-1yl)-4H-1,2,4-triazol-4-yl]-5-chlorobenzyl methanesulfonate

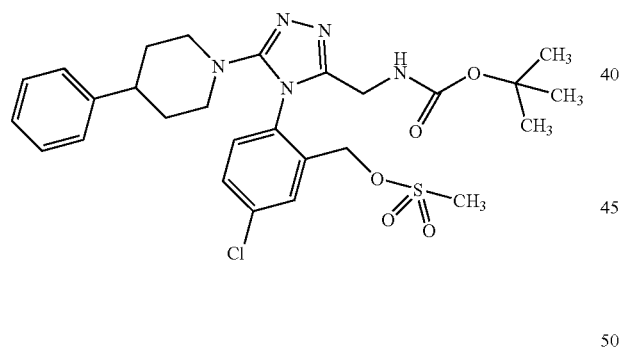

To a stirred solution of the compound from preparation 19 (3.47 g, 6.89 mmol) in dichloromethane (100 mL) was added triethylamine (1.44 mL, 10.33 mmol). The solution was cooled to 0° C. and methanesulfonic anhydride (1.44 g, 8.24 mmol) in dichloromethane (5 mL) was added. The reaction was stirred for 30 minutes. The reaction was diluted with water, the phases were separated and the organic phase was washed with brine, dried over magnesium sulfate and concentrated in vacuo to give the product, 3.74 g (94%).

$^1$H NMR (400 MHz, CDCl$_3$): δ 1.35 (9H, s), 1.50-1.57 (1H, m), 1.65-1.74 (2H, m), 1.85-1.92 (1H, m), 2.56-2.65 (1H, m) 2.80-2.89 (1H, m), 3.02 (3H, s), 3.06-3.15 (1H, m), 3.25-3.31 (1H, m), 3.56-3.75 (1H, m), 3.89-3.92 (2H, m), 4.20-4.24 (2H, m), 5.02 (1H, d), 5.13 (1H, d), 7.14-7.22 (3H, m), 7.28-7.31 (1H, m), 7.36-7.38 (1H, m), 7.53-7.56 (1H, dd), 7.67 (1H, s).

EXAMPLE 1

8-Chloro-1-(4-pyridin-2-ylpiperidin-1-yl)-5,6-dihydro-4H-[1,2,4]triazolo[4,3-a][1,4]benzodiazepine

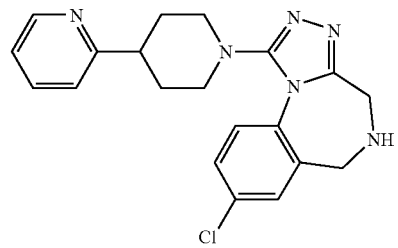

To a stirred solution of the compound from preparation 10 (650 mg, 1.13 mmol) in dioxane (30 mL) was added 4M HCl/dioxane (5 mL). The reaction mixture was stirred for 24 hours at room temperature and the solvent was evaporated in vacuo. The white solid obtained was partitioned between ammonium solution and ethyl acetate. The phases were separated and the aqueous phase was extracted with ethyl acetate (2×20 mL). The organic extracts were combined and washed with brine (20 mL), dried over magnesium sulfate and concentrated in vacuo. Purification by column chromatography on silica gel using dichloromethane:methanol:0.88 ammonia (95:5:0.5) as eluent afforded the product as a white crystalline solid, 752 mg (59%).

$^1$H NMR (400 MHz, CDCl$_3$): δ 1.87-1.98 (4H, m), 2.85 (1H, m), 3.00 (2H, m), 3.52 (2H, m), 3.82 (2H, s), 3.87 (2H, s), 7.09-7.20 (2H, m), 7.42-7.52 (2H, m), 7.63 (1H, m), 7.74 (1H, d), 8.55 (1H, d).

EXAMPLE 2

8-Chloro-5-methyl-1-(4-pyridin-2-ylpiperidin-1-yl)-5,6-dihydro-4H-[1,2,4]triazolo[4,3-a][1,4]benzodiazepine

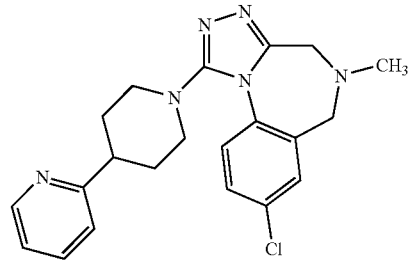

To a stirred solution of the compound from example 1 (100 mg, 0.26 mmol) in dichloromethane (3 mL) was added formaldehyde (37% aqueous solution, 142 μL, 1.75 mmol) followed by sodium triacetoxyborohydride (55 mg, 0.26 mmol). The solution was stirred for 5 hours at room temperature, then sodium triacetoxyborohydride (20 mg, 0.09 mmol) was added. After 10 minutes, saturated sodium hydrogen carbonate solution was added and the mixture was stirred vigorously for 5 minutes. The phases were separated and the organic phase evaporated in vacuo to give the crude residue which was azeotroped twice with ethyl acetate and then diethyl ether to furnish the desired product, 63 mg (61%) as a white solid.

$^1$H NMR (400 MHz, CDCl$_3$): δ 1.94 (4H, m), 2.50 (3H, s), 2.85 (1H, m), 3.01 (2H, m), 3.46 (2H, m), 3.52 (2H, m), 3.62 (2H, s), 7.15 (1H, dd) 7.19 (1H, d), 7.43-7.50 (2H, m), 7.64 (1H, m), 7.74 (1H, d), 8.55 (1H, d).

EXAMPLE 3

8-Chloro-5-(methylsulfonyl)-1-(4-pyridin-2-ylpiperidin-1-yl)-5,6-dihydro-4H-[1,2,4]triazolo[4,3-a][1,4]benzodiazepine

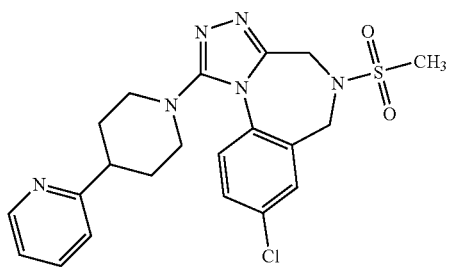

To a stirred solution of the compound from example 1 (100 mg, 0.26 mmol) in dichloromethane (3 mL) was added triethylamine (54.4 μL, 0.39 mmol) at room temperature. The solution was cooled to 0° C. and methanesulfonyl chloride (24 μl, 0.31 mmol) was added. The reaction was stirred for a further 45 minutes. The reaction mixture was then diluted with water (5 mL) and stirred vigorously for 5 minutes. The phases were separated and the organic phase concentrated in vacuo to give the crude residue which was azeotroped with ethyl acetate to afford the product as a crystalline solid, 78 mg (65%).

$^1$H NMR (400 MHz, CDCl$_3$): δ 1.86-2.22 (4H, m), 2.99 (3H, s), 3.03-3.27 (3H, m), 3.60 (2H, m), 4.40 (4H, m), 7.72 (1H, m), 7.82 (1H, m), 7.85-7.99 (3H, m), 8.05 (1H, m), 8.53 (1H, m); LRMS: m/z APCl+459[MH$^+$].

EXAMPLE 4

8-Chloro-5-methyl-1-(4-phenylpiperidin-1-yl)-5,6-dihydro-4H-[1,2,4]triazolo[4,3-a][1,4]benzodiazepine

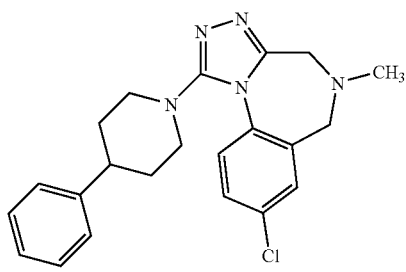

To a stirred solution of the compound from preparation 17 (911 mg, 1.54 mmol) in dioxane (20 mL) was added 4M hydrochloric acid/dioxane (10 mL). The reaction mixture was stirred for 2 hours at room temperature and dioxane was added (20 mL). The mixture was then cooled in an ice-bath and adjusted to pH 9 using triethylamine. It was then heated at 50° C. for 24 hours. The solvent was removed in vacuo to give the crude residue which was suspended in water and extracted with ethyl acetate (2×10 mL). The organic extracts were combined and washed with brine (20 mL), dried over magnesium sulfate and concentrated in vacuo. Purification by column chromatography on silica gel using ethyl acetate and then dichloromethane:methanol (95:5) as eluent gave the desired product as a white crystalline solid, 343 mg (57%).

$^1$H NMR (400 MHz, CDCl$_3$): δ 1.68-1.94 (4H, m), 2.47 (3H, s), 2.66 (1H, m), 2.98 (2H, m), 3.37-3.53 (4H, m), 3.60 (2H, s), 7.21 (3H, m), 7.31 (2H, m), 7.47 (2H, m), 7.72 (1H, d).

EXAMPLE 5

8-Chloro-1-(4-phenylpiperidin-1-yl)-5,6-dihydro-4H-[1,2,4]triazolo[4,3-a][1,4]benzodiazepine

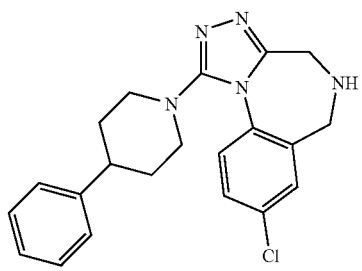

To a stirred solution of the compound from preparation 20 (3.74 g, 6.49 mmol) in dioxane (50 mL) was added 4M HCl/dioxane (26 mL) and the reaction was stirred for 24 hours at room temperature. The solvent was removed in vacuo and the residue partitioned between dichloromethane and 2M sodium hydroxide. The phases were separated and the organic phase was washed with brine (10 mL), dried over magnesium sulfate and evaporated to a yellow gum. The crude residue was redissolved in tetrahydrofuran (100 mL), triethylamine (2.72 mL, 9.76 mmol) was added and the solution was heated under reflux for 20 hours. The solvent was removed in vacuo and the residue was partitioned between water and ethyl acetate. The phases were separated and the aqueous phase was basified with 2M sodium hydroxide solution and extracted with dichloromethane. The organic extracts were combined and washed with brine, dried over magnesium sulfate and concentrated in vacuo to give the crude residue. Purification by column chromatography on silica gel using ethyl acetate and then dichloromethane/methanol/0.8 ammonia (90:10:1) to gave the desired product, 670 mg (27%).

$^1$H NMR (400 MHz, CDCl$_3$): δ 1.72-1.94 (4H, m), 2.66 (1H, m), 3.00 (2H, m), 3.58 (2H, m), 3.81 (2H, s) 3.87 (2H, s), 7.21 (3H, m), 7.31 (2H, m), 7.45-7.54 (2H, m), 7.72 (1H, d).

EXAMPLE 6

8-Chloro-5-(methylsulfonyl)-1-(4-phenylpiperidin-1-yl)-5,6-dihydro-4H-[1,2,4]triazolo[4,3-a][1,4]benzodiazepine

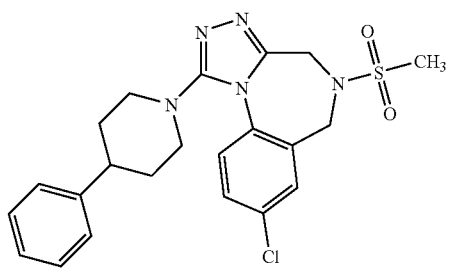

To a stirred solution of the compound from example 5 (200 mg, 0.53 mmol) in dichloromethane (5 mL) was added triethylamine (110 μL, 0.79 mmol). The reaction was cooled to 0° C. and methanesulfonyl chloride (48.9 μL, 0.63 mmol) was added. The solution was stirred for 1 hour at room temperature and diluted with water (5 mL). The phases were separated and the organic phase was washed with brine, dried over magnesium sulfate and concentrated in vacuo and azeotroped with ethyl acetate to give the product as a white crystalline solid, 196 mg (76%).

$^1$H NMR (400 MHz, CDCl$_3$) δ 1.60-1.98 (4H, m), 2.67 (1H, m), 2.84-3.13 (5H, m), 3.48 (2H, s), 4.01-4.59 (4H, m), 7.08-7.40 (5H, m), 7.56 (1H, d), 7.60 (1H, s), 7.76 (1H, d); LRMS: m/z APCl+480[MH$^+$].

EXAMPLE 7

5-Acetyl-8-chloro-1-(4-phenylpiperidin-1-yl)-5,6-dihydro-4H-[1,2,4]triazolo[4,3-a][1,4]benzodiazepine

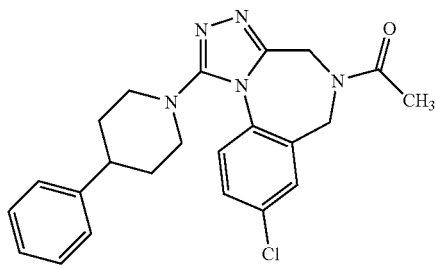

To a stirred solution of the compound from example 5 (200 mg, 0.53 mmol) in dichloromethane (5 mL) was added triethylamine (110 μL, 0.79 mmol). The solution was cooled to 0° C. and acetic anhydride (59.6 μL, 0.63 mmol) was added. The reaction mixture was then stirred for 1 hour, before it was diluted with water (10 mL) and the phases were separated. The organic phase was washed with brine (10 mL), dried over magnesium sulfate and concentrated in vacuo. The residue was azeotroped with ethyl acetate to give the product as a white, crystalline solid, 206 mg (93%)

$^1$H NMR (400 MHz, CDCl$_3$): δ 1.60-1.97 (4H, m), 2.20 (3H, s), 2.67 (1H, m), 3.00 (2H, m), 3.48 (2H, m), 4.28-4.80 (4H, m), 7.07-7.40 (5H, m), 7.40-7.60 (2H, m), 7.79 (1H, d); LRMS: m/z APCl+444[MH$^+$].

EXAMPLE 8

8-Chloro-N,N-dimethyl-1-(4-phenylpiperidin-1-yl)-4H-[1,2,4]triazolo[4,3-a][1,4]benzodiazepine-5(6H)-sulphonamide

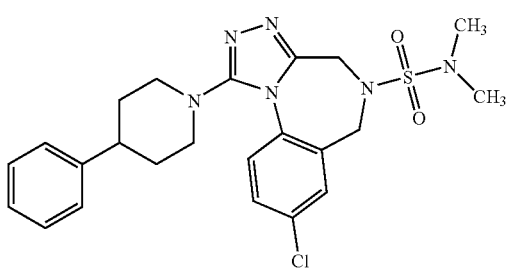

To a stirred solution of the compound from example 5 (270 mg, 0.71 mmol) in dichloromethane (20 mL) was added triethylamine (118.8 μL, 0.86 mmol) followed by dimethylsulfamoyl chloride (84 μL, 0.78 mmol) and the reaction mixture was stirred for 16 hours. Dimethylsulfamoyl chloride (84 μL, 0.78 mmol) was then added and the reaction stirred for a further 72 hours. The reaction was diluted with water (20 mL) and the phases separated. The organic phase was washed with brine, dried over magnesium sulfate and concentrated in vacuo to give the crude residue. Purification by column chromatography on silica gel using ethyl acetate and then dichloromethane methanol (95:5) as eluent gave the product as a white crystalline solid, 217 mg (63%).

$^1$H NMR (400 MHz, CDCl$_3$): δ 1.60-1.95 (4H, m), 2.67 (1H, m), 2.86 (6H, s), 3.01 (2H, m), 3.48 (2H, m), 4.03-4.50 (4H, m), 7.21 (3H, m), 7.32 (2H, m), 7.53 (1H, m), 7.59 (1H, d), 7.74 (1H, d); LRMS: m/z APCl+487[MH$^+$].

EXAMPLE 9

All of the compounds exemplified above showed a Ki value of less than 30 nM when tested in screen 1.0 (V$_{1A}$ filter binding assay) as described above. Examples of specific compounds are illustrated in Table 2 below.

TABLE 2

| Example No. | Ki (nM) |
| --- | --- |
| 3 | 0.62 |
| 6 | 0.17 |
| 8 | 0.36 |

The invention claimed is:

1. A compound of formula (I),

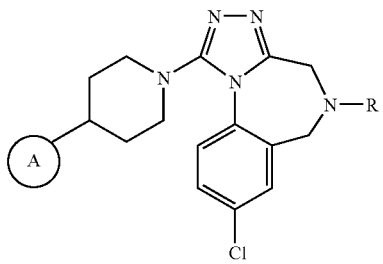

(I)

or a pharmaceutically acceptable salt thereof, wherein
R is H, C$_{1-6}$ alkyl, SO$_2$R$^1$, SO$_2$NR$^1$R$^2$, or COR$^1$;
R$^1$ and R$^2$ are each independently C$_{1-6}$ alkyl; and
Ring A is a phenyl ring or a pyridinyl ring.

2. The compound according to claim 1, or a pharmaceutically acceptable salt thereof, wherein R$^1$ is methyl.

3. The compound according to claim 1 or a pharmaceutically acceptable salt thereof, wherein R$^2$ is methyl.

4. The compound according to claim 1 or a pharmaceutically acceptable salt thereof, wherein Ring A is phenyl.

5. The compound according to claim 1 or a pharmaceutically acceptable salt thereof, wherein Ring A is pyridinyl.

6. A method of treating anxiety, hypertension, primary dysmenorrhea, secondary dysmenorrhea, endometriosis, emesis or premature ejaculation, comprising administering a therapeutically effective amount of a compound according to claim 1 or a pharmaceutically acceptable salt thereof to a patient in need of treatment thereof.

7. The method according to claim 6, wherein primary dysmenorrhea or secondary dysmenorrhea is treated.

8. A pharmaceutical composition comprising a compound according to claim 1 or a pharmaceutically acceptable salt thereof, together with a pharmaceutically acceptable excipient, diluent or carrier.

9. A compound selected from
- 8-Chloro-1-(4-pyridin-2-ylpiperidin-1-yl)-5,6-dihydro-4H-[1,2,4]triazolo[4,3-a][1,4]benzodiazepine;
- 8-Chloro-5-methyl-1-(4-pyridin-2-ylpiperidin-1-yl)-5,6-dihydro-4H-[1,2,4]triazolo[4,3-a][1,4]benzodiazepine;
- 8-Chloro-5-(methylsulfonyl)-1-(4-pyridin-2-ylpiperidin-1-yl)-5,6-dihydro-4H-[1,2,4]triazolo[4,3-a][1,4]benzodiazepine;
- 8-Chloro-5-methyl-1-(4-phenylpiperidin-1-yl)-5,6-dihydro-4H-[1,2,4]triazolo[4,3-a][1,4]benzodiazepine;
- 8-Chloro-1-(4-phenylpiperidin-1-yl)-5,6-dihydro-4H-[1,2,4]triazolo[4,3-a][1,4]benzodiazepine;
- 8-Chloro-5-(methylsulfonyl)-1-(4-phenylpiperidin-1-yl)-5,6-dihydro-4H-[1,2,4]triazolo[4,3-a][1,4]benzodiazepine;
- 5-Acetyl-8-chloro-1-(4-phenylpiperidin-1-yl)-5,6-dihydro-4H-[1,2,4]triazolo[4,3-a][1,4]benzodiazepine; or
- 8-Chloro-N,N-dimethyl-1-(4-phenylpiperidin-1-yl)-4H-[1,2,4]triazolo[4,3-a][1,4]benzodiazepine-5(6H)-sulfonamide;

or a pharmaceutically acceptable salt thereof.

* * * * *